(12) United States Patent
Herrmann et al.

(10) Patent No.: US 12,291,689 B2
(45) Date of Patent: May 6, 2025

(54) COMPOUNDS FOR PROVIDING A LONG-LASTING FLORAL AND FRUITY ODOR

(71) Applicant: FIRMENICH SA, Satigny (CH)

(72) Inventors: Andreas Herrmann, Satigny (CH); Alain Trachsel, Satigny (CH)

(73) Assignee: FIRMENICH SA, Satigny (CH)

( * ) Notice: Subject to any disclaimer, the term of this patent is extended or adjusted under 35 U.S.C. 154(b) by 402 days.

(21) Appl. No.: 17/753,502

(22) PCT Filed: Dec. 17, 2020

(86) PCT No.: PCT/EP2020/086778
§ 371 (c)(1),
(2) Date: Mar. 4, 2022

(87) PCT Pub. No.: WO2021/122997
PCT Pub. Date: Jun. 24, 2021

(65) Prior Publication Data
US 2022/0340837 A1 Oct. 27, 2022

(30) Foreign Application Priority Data
Dec. 19, 2019 (EP) .................................... 19218158

(51) Int. Cl.
*C11B 9/00* (2006.01)
*C07C 317/24* (2006.01)
*C07C 323/22* (2006.01)

(52) U.S. Cl.
CPC .......... *C11B 9/0011* (2013.01); *C07C 317/24* (2013.01); *C07C 323/22* (2013.01); *C11B 9/0034* (2013.01)

(58) Field of Classification Search
CPC ... C11B 9/0011; C11B 9/0034; C11B 9/0015; C11D 3/507; C07C 323/22; C07C 317/24
USPC ........................................................ 512/7, 1
See application file for complete search history.

(56) References Cited

U.S. PATENT DOCUMENTS

| | | | |
|---|---|---|---|
| 2,492,335 A | 12/1949 | Chenicek et al. | |
| 2,794,050 A | 5/1957 | Thompson | |
| 3,040,088 A | 6/1962 | Beachem et al. | |

FOREIGN PATENT DOCUMENTS

| | | | |
|---|---|---|---|
| EP | 3533786 A1 | 9/2019 | |
| WO | 03049666 A2 | 6/2003 | |
| WO | 2008011742 A1 | 1/2008 | |
| WO | 2008142591 A2 | 11/2008 | |
| WO | 2013139766 A1 | 9/2013 | |
| WO | 2016116420 A1 | 7/2016 | |
| WO | 2019243369 A1 | 12/2019 | |

OTHER PUBLICATIONS

Angiolini et al, Sulfur-containing optically active polymers: 2. Synthesis and chiroptical properties of poly(gamma-ketosulfide)s containing the (2R,3R)-1,4-dimercapto-2,3-butanediolbutyraldehyde-acetal moiety, 1993, Polymer, vol. 34, No. 18, 3778-3786 (Year: 1993).*
Manabendra Saha et al, "Solvent-free chemoselective protection of aldehydes on the surface of alumina-sulfuric acid", Green Chemistry Letters and Reviews, Jun. 2011 (Jun. 2011), pp. 137-142, vol. 4, No. 2.
Habib Firouzabadi et al, "H3PW12O40 as a Useful Recyclable Heterogeneous Catalyst for the Facile and Highly Efficient Michael Addition Reaction of Thiols to [alpha],[beta]-Unsaturated Ketones", SYNLETT, Jan. 2005 (Jan. 2005), pp. 299-303, No. 2.
Aurich H G et al, "1,3-Dipolare Cycloaddition von Dinitronen—Bildung tricyclischer Dimerer = 1,3-Dipolar cycloaddition of dinitrones—Formation of tricyclic dimers", Zeitschrift Fur Naturforschung—Section B Journal of Chemical Sciences, Walter De Gruyter GMBH, DE, Jan. 1994 (Jan. 1994), pp. 963-969, vol. 49, No. 7.
Luigi Angiolini et al, "Sulfur-containing optically active polymers: 3. Synthesis and chiroptical properties of optically active poly([gamma]-ketosulfide)s prepared by polyaddition of 1,3-dimercaptobenzene to trans, trans-dibenzylidene acetone in the presence of chiral amines", Polymer, , Mar. 1995 (Mar. 1995), pp. 1071-1082, vol. 36, No. 5.
B.D. Tilak et al, "Synthesis of sulphur heterocyclics-1", Tetrahedron, Jan. 1966 (Jan. 1966), pp. 7-23, vol. 22, No. 1.
Firouzabadi H et al, "Silica gel catalyzed highly selective C—S bond formation via Michael addition of thiols to alpha,beta-unsaturated ketones under solvent-free conditions", Apr. 18, 2006 (Apr. 18, 2006), pp. 98-102, vol. 249, No. 1-2.
H. Surya Prakash Rao et al, "Novel Synthesis of Methyl Ketones Based on the Blaise Reaction", Synthetic Communications, Apr. 15, 2009 (Apr. 15, 2009), pp. 1825-1834, vol. 39, No. 10.
Cemil Ibis et al, "Nucleophilic substitution reactions of 1,4-naphthoquinone and biologic properties of novel S-, S, S-, N-, and N,S-substituted 1,4-naphthoquinone derivatives", Medicinal Chemistry Research, Oct. 10, 2013 (Oct. 10, 2013), pp. 2140-2149, vol. 23, No. 4.
Umberto Maddalena et al, "Thioether Profragrances: Parameters Influencing the Performance of Precursor-Based Fragrance Delivery in Functional Perfumery", Chemistry & Biodiversity, Nov. 2014 (Nov. 2014), pp. 1700-1733, vol. 11, No. 11.

(Continued)

*Primary Examiner* — Jessica Whiteley
(74) *Attorney, Agent, or Firm* — Armstrong Teasdale LLP

(57) ABSTRACT

Described herein are compounds of formula (I) that are able to provide a long-lasting or substantive odor, in particular floral and/or fruity odor, to the environment. Also described herein is a method of imparting a long-lasting odor, in particular a fresh green, floral and/or fruity odor, to surfaces, such as hard surfaces, fabric, skin or hair. Also described herein are a method of using said compounds in perfumery and perfuming compositions or perfumed articles including the compounds described herein.

20 Claims, No Drawings

(56) References Cited

OTHER PUBLICATIONS

Registry Jan. 11, 2001 (Jan. 11, 2001), retrieved from STNDatabase accession No. 313523-81-8; Retrieved from the Internet: URL:Chemical Abstracts Service, XP002798949, Abstract, Columbus, Ohio, US.
Registry Dec. 7, 2000 (Dec. 7, 2000), retrieved from STNDatabase accession No. 307332-26-9; Retrieved from the Internet: URL:Chemical Abstracts Service, XP002798950, Abstract, Columbus, Ohio, US.
International Search Report and Written Opinion for corresponding PCT/EP2020/086778 mailed Mar. 3, 2021; 17 pages.

* cited by examiner

COMPOUNDS FOR PROVIDING A LONG-LASTING FLORAL AND FRUITY ODOR

CROSS-REFERENCE TO RELATED APPLICATIONS

This application is a U.S. National Phase Application of International Patent Application No. PCT/EP2020/086778, filed Dec. 17, 2020, which claims priority to European Patent Application No. 19218158.4, filed Dec. 19, 2019, the entire contents of which are hereby incorporated by reference herein.

TECHNICAL FIELD

The present invention relates to the field of perfumery. The present invention relates to compounds of formula (I) that are able to provide a long-lasting or substantive odor, in particular a fresh green, floral and/or fruity odor, to the environment. Moreover, the present invention relates to a method of imparting a long-lasting odor, in particular a fresh green, floral and/or fruity odor, to surfaces, such as hard surfaces, fabric, skin or hair. Furthermore, the present invention relates to the use of said compounds in perfumery, as well as the perfuming compositions or perfumed articles comprising the invention's compounds.

PRIOR ART

Consumers often correlate the efficiency of perfumed articles with the long-lastingness or substantivity of perfume perception. Perfumes are composed of a multitude of different volatile compounds, which are applied to a surface from which they evaporate to be smelled. The perfume is applied to surfaces, such as hard surfaces, fabric, skin or hair, via a perfume composition or a perfumed consumer article, as for example fine fragrances or diverse washing and cleaning agents. Due to the high volatility of the fragrances, which constitute perfumes, the odor emitted from the perfumed surface can only be perceived over a limited amount of time. In particular the so-called top-notes of a perfume evaporate quite rapidly. They are the most volatile compounds of the composition and represent the freshness of a perfume. Top-notes typically comprise, among others, citrus, flowery, green and fruity notes, and especially the floral and fruity notes are well-appreciated by the consumers. Several classes of floral and fruity notes are used in perfumes. Typical examples of fruity notes are those resembling of cassis, blackcurrant and exotic fruits, as well as of red berries, such as raspberries or strawberries.

Consumers seek for fragrances that are stable in the targeted application and at the same time long-lasting or substantive to be smelled for several hours or even days after application. In particular long-lasting floral and fruity notes are desirable.

Therefore, it is the goal of the present invention to provide a system that is able to deliver a long-lasting or substantive odor, in particular a floral and/or fruity odor, but also other odors, such as fresh green and minty tonalities, to the environment. Furthermore, another objective of the present invention is to find a method of imparting a long-lasting odor, in particular a fresh green, floral and/or fruity odor, to surfaces, such as hard surfaces, fabric, skin or hair, via the application of perfuming compositions or perfumed articles.

DESCRIPTION OF THE INVENTION

We have now found that some specific compounds can advantageously be employed to bring a long-lasting or substantive perfume effect, in particular a fresh green, floral and/or fruity odor note, from a given surface into the environment, and thus to be useful as ingredients for perfuming compositions or perfumed articles.

Therefore, a first aspect of the present invention concerns a compound of formula

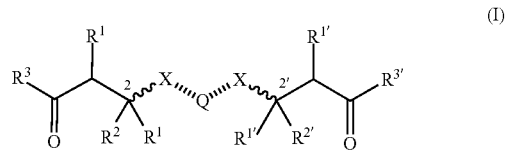

wherein
$R^1$ and $R^{1'}$ represent independently of each other a hydrogen atom or a methyl group; or, both $R^1$ and/or both $R^{1'}$, when taken together, represent a divalent $C_3$ to $C_8$ hydrocarbon group,
$R^2$ and $R^{2'}$ represent independently of each other a hydrogen atom or a $C_1$ to $C_{12}$ hydrocarbon group,
$R^3$ and $R^{3'}$ represent independently of each other a hydrogen atom or a $C_1$ to $C_{16}$ hydrocarbon group;
$R^1$ and $R^3$ and/or $R^{1'}$ and $R^{3'}$ taken together can be connected with a divalent $C_2$ to $C_{12}$ hydrocarbon group,
Q represents a divalent $C_2$ to $C_{22}$ hydrocarbon group, optionally comprising one to eight ether groups and/or one or two functional groups selected from the group consisting of alcohol, ketone, aldehyde, ester, thioether, carboxylic acid, alkali carboxylate, amine, amide, carbamate, nitrile or thiol; and
each X represents independently of each other either one of the groups of formulae (i) to (iii)

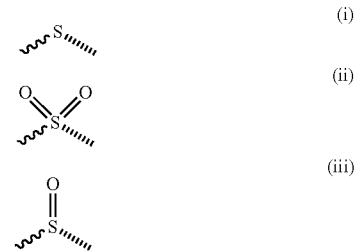

wherein the wavy line indicates the location of the bond between carbons 2 and 2' and X and the hatched line indicates the location of the bond between X and Q, provided that the hatched line is not directly linked to a heteroatom or to a carbonyl functional group of Q.

It is understood that by " . . . hydrocarbon group . . . " it is meant that said group consists of hydrogen and carbon atoms and can be in the form of an aliphatic hydrocarbon, i.e. linear or branched saturated hydrocarbon (e.g. alkyl group), a linear or branched unsaturated hydrocarbon (e.g. alkenyl or alkynyl group), a saturated cyclic hydrocarbon (e.g. cycloalkyl) or an unsaturated cyclic hydrocarbon (e.g. cycloalkenyl or cycloalkynyl), or can be in the form of an aromatic hydrocarbon, i.e. aryl group, or can also be in the form of a mixture of said type of groups, e.g. a specific group may comprise a linear alkyl, a branched alkenyl (e.g. having one or more carbon-carbon double bonds), a (poly)cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

It is understood that with the terms " . . . a hydrocarbon group, optionally comprising . . . " and " . . . a hydrocarbon group, optionally substituted with . . . " it is meant that said hydrocarbon group optionally comprises alcohol, ketone, aldehyde, ether, thioether, ester, carboxylic acid, alkali carboxylate, amine, amide, carbamate, nitrile or thiol groups. These groups can either substitute a hydrogen atom of the hydrocarbon group and thus be laterally attached to said hydrocarbon, or substitute a carbon atom (if chemically possible) of the hydrocarbon group and thus be inserted into the hydrocarbon chain. For example, a —$CH_2$—$CH_2$—CHOH—$CH_2$— group represents a $C_4$ hydrocarbon group comprising an alcohol group (substitution of a hydrogen atom), a —$CH_2$—$CH_2$—COO—$CH_2$—$CH_2$—OCO—$CH_2$—$CH_2$— group represents a $C_6$ hydrocarbon group comprising two ester groups (substitution of carbon atoms/insertion into the hydrocarbon chain) and, similarly, a —$CH_2$—$CH_2$—O—$CH_2$—$CH_2$—O—$CH_2$—$CH_2$— group represents a $C_6$ hydrocarbon group comprising two ether groups.

In an embodiment of the invention, the two X groups attached to Q are separated from each other by at least four carbon atoms.

The term "the two X groups attached to Q are separated from each other by at least four carbon atoms" means that there are at least four different carbon atoms of Q between one X group and the second X group. These four carbon atoms can be part of any substituted or unsubstituted, hydrocarbon group, provided that the shortest possible path for moving from one X group to the other X group passes through at least four different carbon atoms of Q.

In a preferred embodiment, the two X groups attached to Q are separated from each other by at least five, preferably six carbon atoms.

According to any embodiment of the invention, all $R^1$ and $R^{1'}$, $R^2$ and $R^{2'}$, and $R^3$ and $R^{3'}$ in formula (I) may be different, preferably, $R^1$ and $R^{1'}$, $R^2$ and $R^{2'}$, and $R^3$ and $R^{3'}$ in formula (I) are pairwise the same.

It is herein understood by the expression "$R^1$ and $R^{1'}$ represent independently" that each (of the two) $R^1$ and each (of the two) $R^{1'}$ represent independently from each other the indicated substituents, i.e. a hydrogen atom or a methyl group; or, both $R^1$ and/or both $R^{1'}$, when taken together, represent a divalent $C_3$ to $C_8$ hydrocarbon group. In other words, $R^1$ alpha to the carbonyl group may be a hydrogen atom or a methyl group while the $R^1$ geminal to $R^2$ may be independently thereof a hydrogen or a methyl group and $R^{1'}$ alpha to the carbonyl group may be a hydrogen atom or a methyl group while $R^{1'}$ geminal to $R^{2'}$ may be independently thereof a hydrogen or a methyl group; or, both $R^1$ and/or both $R^{1'}$, when taken together, represent a divalent $C_3$ to $C_8$ hydrocarbon group. In a particular embodiment, both $R^1$ represent a hydrogen atom or a methyl group and independently thereof both $R^{1'}$ represent a hydrogen atom or a methyl group; or, both $R^1$ and/or both $R^{1'}$, when taken together, represent a divalent $C_3$ to $C_8$ hydrocarbon group.

According to any embodiment of the invention, $R^1$ and $R^{1'}$ each independently may preferably represent a hydrogen atom or a methyl group, preferably $R^1$ and $R^{1'}$ each independently may be a hydrogen atom.

According to any embodiment of the invention, $R^2$ and $R^{2'}$ each independently may preferably represent a $C_1$ to $C_{12}$ hydrocarbon group, even more preferably a $C_1$ to $C_{10}$ hydrocarbon group, preferably, $R^2$ and $R^{2'}$ each independently may be a methyl group, an ethyl group, a $C_6$ to $C_{10}$ alkyl or alkenyl group or a $C_5$ to $C_{10}$ cycloalkyl or cycloalkenyl group optionally substituted by one to three $C_1$ to $C_3$ alkyl or $C_2$ to $C_3$ alkenyl, preferably, $R^2$ and $R^{2'}$ each independently may be a methyl group, an ethyl group or a $C_6$ to $C_{10}$ alkyl or alkenyl group, even more preferably, $R^2$ and $R^{2'}$ each independently may be a methyl group.

According to a particular embodiment, $R^2$ and/or $R^{2'}$ each independently may preferably represent a hydrogen atom when both $R^1$ and/or both $R^{1'}$, when taken together, represent a divalent $C_3$ to $C_8$ hydrocarbon group or when $R^1$, geminal to $R^2$, and $R^3$ and/or $R^{1'}$, geminal to $R^{2'}$, and $R^{3'}$ taken together can be connected with a divalent $C_2$ to $C_{12}$ hydrocarbon group. In other words, $R^2$ and/or $R^{2'}$ each independently may not represent a hydrogen atom when the at least one molecule to be released does not comprise a ring; i.e. both $R^1$ and/or both $R^{1'}$ taken together or $R^1$, geminal to $R^2$, and $R^3$ and/or $R^{1'}$, geminal to $R^{2'}$, and $R^{3'}$ taken together form a ring.

According to any embodiment of the invention, $R^3$ and $R^{3'}$ each independently may preferably represent a hydrogen atom or a $C_1$ to $C_{10}$ hydrocarbon group, $R^3$ and $R^{3'}$ each independently may represent a $C_1$ to $C_9$ hydrocarbon group, even more preferably $R^3$ and $R^{3'}$ each independently may represent a $C_4$ hydrocarbon group and most preferably $R^3$ and $R^{3'}$ each independently may represent an n-butyl group.

According to any embodiment of the invention, $R^1$ and $R^3$ and/or $R^{1'}$ and $R^{3'}$, when taken together, may preferably represent a divalent $C_2$ to $C_6$ hydrocarbon group.

According to any embodiment of the invention, both $R^1$ and/or both $R^{1'}$, when taken together, may form a $C_{5-8}$ cycloakyl group or a $C_{5-8}$ cycloalkenyl group, each optionally substituted by one to three $C_{1-8}$ alkyl groups or $C_{1-8}$ alkenyl groups.

The terms "alkyl" and "alkenyl" are understood as comprising branched and linear alkyl and alkenyl groups. The terms "alkenyl" and "cycloalkenyl" are understood as comprising 1, 2 or 3 olefinic double bonds, preferably 1 or 2 olefinic double bonds. The terms "cycloalkyl" and "cycloalkenyl" are understood as comprising monocyclic or fused, spiro and/or bridged bicyclic or tricyclic cycloalkyl and cycloalkenyl groups, preferably monocyclic cycloalkyl and cycloalkenyl groups.

According to any embodiment of the invention, Q may preferably represent a divalent $C_4$ to $C_{22}$, preferably $C_4$ to $C_{18}$, more preferably $C_5$ to $C_{18}$, hydrocarbon group optionally comprising one to eight ether groups and/or with one or two functional groups selected from the group consisting of alcohol, ketone, aldehyde, ester, carboxylic acid, amine, amide or carbamate. Preferably, Q may represent a divalent $C_2$ to $C_{18}$, preferably $C_4$ to $C_{18}$, more preferably $C_5$ to $C_{18}$, alkyl or alkenyl group, optionally comprising one to six ether groups and/or with one or two functional groups selected from the group consisting of alcohol, ester, carboxylic acid, amine, or carbamate. Preferably, Q may represent a divalent $C_3$ to $C_{16}$, preferably $C_4$ to $C_{16}$, more preferably $C_5$ to $C_{16}$, alkyl or alkenyl group, optionally comprising one to four ether groups, or a divalent $C_4$ to $C_{12}$ alkyl group, optionally comprising one to four ether groups. More preferably Q may represent a divalent $C_2$ to $C_{16}$, preferably $C_4$ to $C_{16}$, more preferably $C_5$ to $C_{16}$ alkyl, $C_2$ to $C_{16}$, preferably $C_4$ to $C_{16}$, more preferably $C_5$ to $C_{16}$ alkenyl or a $C_4$ to $C_{16}$ mono-, di-, tri- or tetraoxoalkyl group.

According to a particular embodiment, Q may represent a divalent butyl, pentyl, hexyl, heptyl, octyl, nonyl, decyl, undecyl, dodecyl, 3-oxapentyl, 3,6-dioxaoctyl, 3,6,9-trioxaundecyl, 3,6,9,12-tetraoxatetradecyl, even more preferably Q may represent a divalent hexyl, octyl, decyl, dodecyl, 3-oxapentyl, 3,6-dioxaoctyl, 3,6,9-trioxaundecyl or 3,6,9,12-tetraoxatetradecyl group, even more preferably Q may represent a divalent 3,6 dioxaoctyl group.

According to any embodiment of the invention, each X may preferably represent the same group selected among formulae (i) to (iii).

According to any embodiment of the invention, preferably each X may independently represent a group of formula (i) or (ii), most preferably a group of formula (i).

According to a particular embodiment, $R^1$ and $R^{1'}$ may represent a hydrogen atom or a methyl group, $R^2$ and $R^{2'}$ may represent a methyl or an ethyl group and $R^3$ and $R^{3'}$ may represent a hydrogen atom or a $C_1$ to $C_{10}$ hydrocarbon group, $R^1$ and $R^3$ and/or $R^{1'}$ and $R^{3'}$, when taken together, may represent a divalent $C_2$ to $C_6$ hydrocarbon group, X may represent the groups of formula (i) and/or (ii) and Q may represent a divalent $C_2$ to $C_{16}$, preferably $C_4$ to $C_{18}$ alkyl or alkenyl group, optionally comprising one to four ether groups and/or with one or two functional groups selected from the group consisting of ester, alcohol, amine or carbamate.

In a particular embodiment of the invention, the following compounds are excluded from the compound of formula (I): 3,3'-(ethane-1,2-diylbis(sulfanediyl))dipropanal, 3,3'-(propane-1,3-diylbis(sulfanediyl))dipropanal, 3,3'-(butane-1,4-diylbis(sulfanediyl))dipropanal, 3,3'-((oxybis(ethane-2,1-diyl))bis(sulfanediyl))dipropanal, ethane-1,2-diyl bis(2-((3-oxopropyl)thio)acetate), 3,3'-(butane-1,4-diyldisulfonyl) dipropanal, 4,4'-(ethane-1,2-diylbis(sulfanediyl))bis(butan-2-one), 4,4'-(propane-1,3-diylbis(sulfanediyl))bis(butan-2-one), 4,4'-(butane-1,4-diyldisulfonyl)bis(butan-2-one), 4,4'-(propane-2,2-diylbis(sulfanediyl))bis(butan-2-one), 4,4'-(propane-2,2-diylbis(sulfanediyl))bis(4-methylpentan-2-one), 4,4'-(propane-2,2-diylbis(sulfanediyl))bis(4-methylhexan-2-one), 4,4'-(butane-2,2-diylbis(sulfanediyl))bis(4-methylpentan-2-one), 4,4'-(pentane-3,3-diylbis (sulfanediyl))bis(4-methylpentan-2-one), 4,4'-(pentane-2,2-diylbis(sulfanediyl))bis(4-methylpentan-2-one), 4,4'-(heptane-3,3-diylbis(sulfanediyl))bis(4-methylpentan-2-one), 1,1'-(propane-2,2-diylbis(sulfanediyl))bis(hex-5-en-3-one), 1,1'-(heptane-3,3-diylbis(sulfanediyl))bis(hex-5-en-3-one), 1,1'-(propane-2,2-diylbis(sulfanediyl))bis(hept-5-en-3-one), 3,3'-(propane-2,2-diylbis(sulfanediyl))bis(1-cyclohexylpropan-1-one), 3,3'-(hexane-2,2-diylbis (sulfanediyl))bis(1-cyclohexylpropan-1-one), 5,5'-(propane-2,2-diylbis(sulfanediyl))bis(1-cyclohexylpentan-3-one), 3,3'-(propane-2,2-diylbis(sulfanediyl))bis(1-phenylpropan-1-one), 3,3'-(propane-2,2-diylbis(sulfanediyl))bis(1-(naphthalen-2-yl)propan-1-one), 3,3'-(propane-2,2-diylbis(sulfanediyl))bis(1,3-diphenylpropan-1-one), 4,4'-(methylenebis(sulfanediyl))bis(4-phenylbutan-2-one), 3,3'-(propane-2,2-diylbis(sulfanediyl))bis(1,3-diphenylbutan-1-one), 3,3'-(propane-2,2-diylbis(sulfanediyl))bis(1-(p-tolyl) propan-1-one), 3,3'-(propane-2,2-diylbis(sulfanediyl))bis(1-(3,5-dimethylphenyl)propan-1-one), 3,3'-(propane-2,2-diylbis(sulfanediyl))dipropanal, 3,3'-(propane-2,2-diylbis (sulfanediyl))dibutanal, 3,3'-(propane-2,2-diylbis (sulfanediyl))bis(3-phenylpropanal), 4,4'-((phenylmethylene)bis(sulfanediyl))bis(butan-2-one), 4,4'-((phenylmethylene)bis(sulfanediyl))bis(4-methylpentan-2-one), 3,3'-(butane-1,1-diylbis(sulfanediyl))dipropanal, 3,3'-((phenylmethylene)bis(sulfanediyl))bis(3-phenylpropanal), 4,4'-(butane-1,1-diylbis(sulfanediyl))bis(4-methylpentan-2-one), 3,3'-(ethane-1,2-diylbis(sulfanediyl))bis(cyclopentan-1-one), 3,3'-(propane-1,3-diylbis(sulfanediyl))bis(cyclopentan-1-one), 3,3'-(ethane-1,2-diylbis(sulfanediyl))bis (cyclohexan-1-one), 3,3'-((propane-1,3-diylbis (sulfanediyl))bis(methylene))bis(cyclohexan-1-one), 4,4'-(naphthalene-1,5-diylbis(sulfanediyl))bis(butan-2-one), 3,3'-(propane-2,2-diylbis(sulfanediyl))bis(1-cyclohexylpropan-1-one), 4,4'-(1,3-phenylenebis(sulfanediyl))bis(4-phenylbutan-2-one), 3,3'-(ethane-1,2-diylbis(sulfanediyl))bis(1,3-diphenylpropan-1-one), 2,3-bis((2-(4-methyl-2-oxocyclohexyl)propan-2-yl)thio)naphthalene-1,4-dione, 4,4'-(methylenebis(4,1-phenylenesulfonyl))bis(4-methylpentan-2-one) and 4,4'-([1,1'-biphenyl]-4,4'-disulfonyl)bis (4-methylpentan-2-one). Particularly, the following compounds are excluded from the compound of formula (I): 4,4'-(methylenebis(4,1-phenylenesulfonyl))bis(4-methylpentan-2-one) and 4,4'-([1,1'-biphenyl]-4,4'-disulfonyl)bis (4-methylpentan-2-one)

In a particular embodiment of the invention, the following compounds are excluded from formula (I): ethane-1,2-diyl bis(2-((4-oxooctan-2-yl)thio)acetate).

In a particular embodiment of the invention, the following compounds are excluded from formula (I): $C_{2-20}$ alkyl-1,2-diyl bis(2-((4-oxooctan-2-yl)thio)acetate), $C_{2-20}$ alkyl-1,2-diyl bis(2-((4-oxooctan-2-yl)sulfinyl)acetate) and/or $C_{2-20}$ alkyl-1,2-diyl bis(2-((4-oxooctan-2-yl)sulfonyl)acetate).

According to an embodiment, the compound of formula (I) may be a homo-dimer or a hetero-dimer. By homo-dimer it is herein understood that the two substituents attached to X (and not comprising Q) have the same chemical structure. By hetero-dimer it is herein understood that the two substituents attached to X (and not comprising Q) have a different chemical structure. In other words, the $R^3C(=O)$ $CHR^1CR^2R^1$ group and $R^{3'}C(=O)CHR^{1'}CR^{2'}R^{1'}$ group may be identic or different, respectively being homo-dimer or hetero-dimer.

According to any embodiment of the invention, the compound of formula (I) is preferably a compound of formula

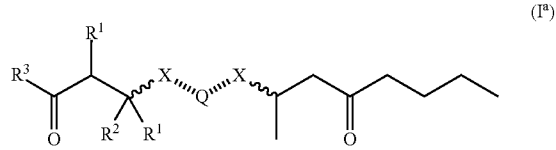

(I$^a$)

wherein $R^1$, $R^2$, $R^3$, X and Q have the same meaning as indicated in formula (I), even more preferably, the compound of formula (I) is a compound of formula

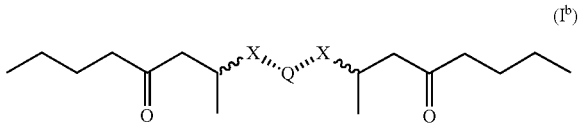

(I$^b$)

wherein X and Q have the same meaning as indicated for the compound of formula (I).

According to any one of the above embodiments, said compound of formula (I) is a 2,2'-(alkane-α,ω-diylbis(sulfanediyl))bis(octan-4-one) with the size of the alkyl group varying between $C_4$ and $C_{22}$, preferably between $C_4$ and $C_{18}$, even more preferably between $C_5$ and $C_{16}$, such as 2,2'-(hexane-1,6-diylbis(sulfanediyl))bis(octan-4-one), 2,2'-(heptane-1,7-diylbis(sulfanediyl))bis(octan-4-one), 2,2'-(octane-1,8-diylbis(sulfanediyl))bis(octan-4-one), 2,2'-(nonane-1,9-diylbis(sulfanediyl))bis(octan-4-one), 2,2'-(decane-1,10-diylbis(sulfanediyl))bis(octan-4-one), 2,2'-(undecane-1,11-diylbis(sulfanediyl))bis(octan-4-one) or 2,2'-(dodecane-1,12-diylbis(sulfanediyl))bis(octan-4-one), a 2,2'-(oxaalkane-α,ω-diylbis(sulfanediyl))bis(octan-4-one) with the size of the alkyl group varying between $C_4$ and $C_{22}$, preferably between $C_4$ and $C_{18}$, even more preferably between $C_4$ and $C_{12}$ and with the alkyl group comprising one to four ether groups, such as 2,2'-(3-oxapentane-1,5-diylbis(sulfanediyl))bis(octan-4-one), 2,2'-(3,6-dioxaoctane-1,8-diylbis(sulfanediyl))bis(octan-4-one), 2,2'-(3,6,9-trioxaundecane-1,11-diylbis(sulfanediyl))bis(octan-4-one) or 2,2'-(3,6,9,12-tetraoxatetradecane-1,14-diylbis(sulfanediyl))bis(octan-4-one), a 2,2'-(alkane-α,ω-diyldisulfonyl)bis(octan-4-one), with the size of the alkyl group varying between $C_4$ and $C_{22}$, preferably between $C_4$ and $C_{18}$, even more preferably between $C_5$ and $C_{16}$, such as 2,2'-(hexane-1,6-diyldisulfonyl)bis(octan-4-one), 2,2'-(heptane-1,7-diyldisulfonyl)bis(octan-4-one), 2,2'-(octane-1,8-diyldisulfonyl)bis(octan-4-one), 2,2'-(nonane-1,9-diyldisulfonyl)bis(octan-4-one), 2,2'-(decane-1,10-diyldisulfonyl)bis(octan-4-one), 2,2'-(undecane-1,11-diyldisulfonyl)bis(octan-4-one) or 2,2'-(dodecane-1,12-diyldisulfonyl)bis(octan-4-one) or a 2,2'-(oxaalkane-α,ω-diyldisulfonyl)bis(octan-4-one) with the size of the alkyl group varying between $C_4$ and $C_{22}$, preferably between $C_4$ and $C_{16}$, even more preferably between $C_4$ and $C_{12}$ and with the alkyl group comprising one to four ether groups, such as 2,2'-(3-oxapentane-1,5-diyldisulfonyl)bis(octan-4-one), 2,2'-(3,6-dioxaoctane-1,8-diyldisulfonyl)bis(octan-4-one), 2,2'-(3,6,9-trioxaundecane-1,11-diyldisulfonyl)bis(octan-4-one) or 2,2'-(3,6,9,12-tetraoxatetradecane-1,14-diyldisulfonyl)bis(octan-4-one).

According to any embodiment of the invention, the compound of formula (I) is preferably a compound of formula

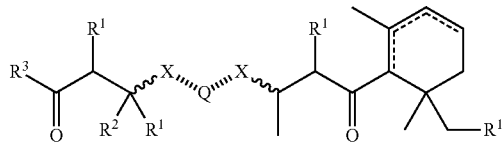

(I$^c$)

wherein $R^1$, $R^2$, $R^3$, X and Q have the same meaning as indicated in formula (I), and wherein the dotted lines represent the location of a single or a double bond, even more preferably, the compound of formula (I) is a compound of formula

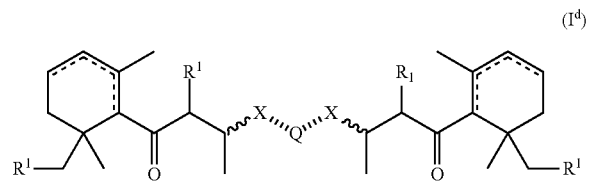

(I$^d$)

wherein $R^1$, X and Q have the same meaning as indicated for the compound of formula (I), and wherein the dotted lines represent the location of a single or a double bond.

According to any one of the above embodiments, said compound of formula (I) is 3,3'-(alkane-α,ω-diylbis(sulfanediyl))bis(1-(2,6,6-trimethylcyclohex-1-, 2- or 3-en-1-yl)butan-1-one), 3,3'-(alkane-α,ω-diylbis(sulfanediyl))bis(1-(6-ethyl-2,6-dimethylcyclohex-3-en-1-yl)butan-1-one), 3,3'-(alkane-α,ω-diylbis(sulfanediyl))bis(2-methyl-1-(2,6,6-trimethylcyclohex-1-, 2- or 3-en-1-yl)butan-1-one) or 3,3'-(alkane-α,ω-diylbis(sulfanediyl))bis(1-(2,6,6-trimethylcyclohex-1,3-dien-1-yl)butan-1-one) with the size of the alkyl group varying between $C_4$ and $C_{22}$, preferably between $C_4$ and $C_{18}$, even more preferably between $C_5$ and $C_{16}$, such as 3,3'-(hexane-1,6-diylbis(sulfanediyl))bis(1-(2,6,6-trimethylcyclohex-1-, 2- or 3-en-1-yl)butan-1-one), 3,3'-(hexane-1,6-diylbis(sulfanediyl))bis(1-(6-ethyl-2,6-dimethylcyclohex-3-en-1-yl)butan-1-one), 3,3'-(hexane-1,6-diylbis(sulfanediyl))bis(2-methyl-1-(2,6,6-trimethylcyclohex-1-, 2- or 3-en-1-yl)butan-1-one), 3,3'-(hexane-1,6-diylbis(sulfanediyl))bis(1-(2,6,6-trimethylcyclohex-1,3-dien-1-yl)butan-1-one), 3,3'-(heptane-1,7-diylbis(sulfanediyl))bis(1-(2,6,6-trimethylcyclohex-1-, 2- or 3-en-1-yl)butan-1-one), 3,3'-(octane-1,8-diylbis(sulfanediyl))bis(1-(2,6,6-trimethylcyclohex-1-, 2- or 3-en-1-yl)butan-1-one), 3,3'-(nonane-1,9-diylbis(sulfanediyl))bis(1-(2,6,6-trimethylcyclohex-1-, 2- or 3-en-1-yl)butan-1-one), 3,3'-(decane-1,10-diylbis(sulfanediyl))bis(1-(2,6,6-trimethylcyclohex-1-, 2- or 3-en-1-yl)butan-1-one), 3,3'-(undecane-1,11-diylbis(sulfanediyl))bis(1-(2,6,6-trimethylcyclohex-1-, 2- or 3-en-1-yl)butan-1-one) or 3,3'-(dodecane-1,12-diylbis(sulfanediyl))bis(1-(2,6,6-trimethylcyclohex-1-, 2- or 3-en-1-yl)butan-1-one), 3,3'-(oxaalkane-α,ω-diylbis(sulfanediyl))bis(1-(2,6,6-trimethylcyclohex-1-, 2- or 3-en-1-yl)butan-1-one), 3,3'-(oxaalkane-α,ω-diylbis(sulfanediyl))bis(1-(6-ethyl-2,6-dimethylcyclohex-3-en-1-yl)butan-1-one), 3,3'-(oxaalkane-α,ω-diylbis(sulfanediyl))bis(2-methyl-1-(2,6,6-trimethylcyclohex-1-, 2- or 3-en-1-yl)butan-1-one) or 3,3'-(oxaalkane-α,ω-diylbis(sulfanediyl))bis(1-(2,6,6-trimethylcyclohex-1,3-dien-1-yl)butan-1-one) with the size of the alkyl group varying between $C_4$ and $C_{22}$, preferably between $C_4$ and $C_{16}$, even more preferably between $C_4$ and $C_{12}$ and with the alkyl group comprising one to four ether groups, such as 3,3'-(3-oxapentane-1,5-diylbis(sulfanediyl))bis(1-(2,6,6-trimethylcyclohex-1-, 2- or 3-en-1-yl)butan-1-one), 3,3'-(3,6-dioxaoctane-1,8-diylbis(sulfanediyl))bis(1-(2,6,6-trimethylcyclohex-1-, 2- or 3-en-1-yl)butan-1-one), 3,3'-(3,6-dioxaoctane-1,8-diylbis(sulfanediyl))bis(1-(6-ethyl-2,6-dimethylcyclohex-3-en-1-yl)butan-1-one), 3,3'-(3,6-dioxaoctane-1,8-diylbis(sulfanediyl))bis(2-methyl-1-(2,6,6-trimethylcyclohex-1-, 2- or 3-en-1-yl)butan-1-one), 3,3'-(3,6-dioxaoctane-1,8-diylbis(sulfanediyl))bis(1-(2,6,6-trimethylcyclohex-1,3-dien-1-yl)butan-1-one), 3,3'-(3,6,9-trioxaundecane-1,11-diylbis(sulfanediyl))bis(1-(2,6,6-trimethylcyclohex-1-, 2- or 3-en-1-yl)butan-1-one) or 3,3'-(3,6,9,12-tetraoxatetradecane-1,14-diylbis(sulfanediyl))bis(1-(2,6,6-trimethylcyclohex-1-, 2- or 3-en-1-yl)butan-1-one), 3,3'-(alkane-α,ω-diyldisulfonyl)bis(1-(2,6,6-trimethylcyclohex-1-, 2- or 3-en-1-yl)butan-1-one), 3,3'-(alkane-α,ω-diyldisulfonyl)bis(1-(6-ethyl-2,6-dimethylcyclohex-3-en-1-yl)butan-1-one), 3,3'-(alkane-α,ω-diyldisulfonyl)bis(2-methyl-1-(2,6,6-trimethylcyclohex-1-, 2- or 3-en-1-yl)butan-1-one) or a 3,3'-(alkane-α,ω-diyldisulfonyl)bis(1-(2,6,6-trimethylcyclohex-1,3-dien-1-yl)butan-1-one), with the size of the alkyl group varying between $C_4$ and $C_{22}$, preferably between $C_4$ and $C_{18}$, even more preferably between $C_5$ and $C_{16}$, such as 3,3'-(hexane-1,6-diyldisulfonyl)bis(1-(2,6,6-trimethylcyclohex-1-, 2- or 3-en-1-yl)butan-1-one), 3,3'-(hexane-1,6-diyldisulfonyl)bis(1-(6-ethyl-2,6-dimethylcyclohex-3-en-1-yl)butan-1-one), 3,3'-(hexane-1,6-diyldisulfonyl)bis(2-methyl-1-(2,6,6-trimethylcyclohex-1-, 2- or 3-en-1-yl)butan-1-one), 3,3'-(hexane-1,6-diyldisulfonyl)bis(1-(2,6,6-trimethylcyclohex-1,3-dien-1-yl)butan-1-one), 3,3'-(heptane-1,7-diyldisulfonyl)bis(1-(2,6,6-trimethylcyclohex-1-, 2- or 3-en-1-yl)butan-1-one), 3,3'-(octane-1,8-diyldisulfonyl)bis(1-(2,6,6-trimethylcyclohex-1-, 2- or 3-en-1-yl)butan-1-one), 3,3'-(nonane-1,9-diyldisulfonyl)bis(1-(2,6,6-trimethylcyclohex-1-, 2- or 3-en-1-yl)butan-1-one), 3,3'-(decane-1,10-diyldisulfonyl)bis(1-(2,6,6-trimethylcyclohex-1-, 2- or 3-en-1-yl)butan-1-one), 3,3'-(undecane-1,11-diyldisulfonyl)bis(1-(2,6,6-trimethylcyclohex-1-, 2- or 3-en-1-yl)butan-1-one) or 3,3'-(dodecane-1,12-diyldisulfonyl)bis(1-(2,6,6-trimethylcyclohex-1-, 2- or 3-en-1-yl)butan-1-one) or 3,3'-(oxaalkane-α,ω-diyldisulfonyl)bis(1-(2,6,6-trimethylcyclohex-1-, 2- or 3-en-1-yl)butan-1-one), 3,3'-(oxaalkane-α,ω-diyldisulfonyl)bis(1-(6-ethyl-2,6-dimethylcyclohex-3-en-1-yl)butan-1-one), 3,3'-(oxaalkane-α,ω-diyldisulfonyl)bis(2-methyl-1-(2,6,6-trimethylcyclohex-1-, 2- or 3-en-1-yl)butan-1-one) or a 3,3'-(oxaalkane-α,ω-diyldisulfonyl)bis(1-(2,6,6-trimethylcyclohex-1,3-dien-1-yl)butan-1-one), with the size of the alkyl group varying between $C_4$ and $C_{22}$, preferably between $C_4$ and $C_{16}$, even more preferably between $C_4$ and $C_{12}$ and with the alkyl group comprising one to four ether groups, such as 3,3'-(3-oxapentane-1,5-diyldisulfonyl)bis(1-(2,6,6-trimethylcyclohex-1-, 2- or 3-en-1-yl)butan-1-one), 3,3'-(3,6-dioxaoctane-1,8-diyldisulfonyl)bis(1-(2,6,6-trimethylcyclohex-1-, 2- or 3-en-1-yl)butan-1-one), 3,3'-(3,6-dioxaoctane-1,8-diyldisulfonyl)bis(1-(6-ethyl-2,6-dimethylcyclohex-3-en-1-yl)butan-1-one), 3,3'-(3,6-dioxaoctane-1,8-diyldisulfonyl)bis(2-methyl-1-(2,6,6-trimethylcyclohex-1-, 2- or 3-en-1-yl)butan-1-one), 3,3'-(3,6-dioxaoctane-1,8-diyldisulfonyl)bis(1-(2,6,6-trimethylcyclohex-1,3-dien-1-yl)butan-1-one), 3,3'-(3,6,9-trioxaundecane-1,11-diyldisulfonyl)bis(1-(2,6,6-trimethylcyclohex-1-, 2- or 3-en-1-yl)butan-1-one) or 3,3'-(3,6,9,12-tetraoxatetradecane-1,14-diyldisulfonyl)bis(1-(2,6,6-trimethylcyclohex-1-, 2- or 3-en-1-yl)butan-1-one).

According to any embodiment of the invention, the compound of formula (I) is preferably a compound of formula

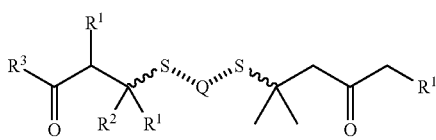

(I$^e$)

wherein $R^1$, $R^2$, $R^3$ and Q have the same meaning as indicated in formula (I), even more preferably, the compound of formula (I) is a compound of formula

(I$^f$)

wherein Q has the same meaning as indicated for the compound of formula (I).

According to any one of the above embodiments, said compound of formula (I) is a 4,4'-(alkane-α,ω-diylbis(sulfanediyl))bis(4-methylpentan-2-one) with the size of the alkyl group varying between $C_4$ and $C_{22}$, preferably between $C_4$ and $C_{18}$, even more preferably between $C_5$ and $C_{16}$, such as 4,4'-(hexane-1,6-diylbis(sulfanediyl))bis(4-methylpentan-2-one), 4,4'-(heptane-1,7-diylbis(sulfanediyl))bis(4-methylpentan-2-one), 4,4'-(octane-1,8-diylbis(sulfanediyl))bis(4-methylpentan-2-one), 4,4'-(nonane-1,9-diylbis(sulfanediyl))bis(4-methylpentan-2-one), 4,4'-(decane-1,10-diylbis(sulfanediyl))bis(4-methylpentan-2-one), 4,4'-(undecane-1,11-diylbis(sulfanediyl))bis(4-methylpentan-2-one) or 4,4'-(dodecane-1,12-diylbis(sulfanediyl))bis(4-methylpentan-2-one) or a 4,4'-(oxaalkane-α,ω-diylbis(sulfanediyl))bis(4-methylpentan-2-one) with the size of the alkyl group varying between $C_4$ and $C_{22}$, preferably between $C_4$ and $C_{16}$, even more preferably between $C_4$ and $C_{12}$ and with the alkyl group comprising one to four ether groups, such as 4,4'-(3-oxapentane-1,5-diylbis(sulfanediyl))bis(4-methylpentan-2-one), 4,4'-(3,6-dioxaoctane-1,8-diylbis(sulfanediyl))bis(4-methylpentan-2-one), 4,4'-(3,6,9-trioxaundecane-1,11-diylbis(sulfanediyl))bis(4-methylpentan-2-one) or 4,4'-(3,6,9,12-tetraoxatetradecane-1,14-diylbis(sulfanediyl))bis(4-methylpentan-2-one).

The compounds according to formula (I) are able to slowly generate α,β-unsaturated aldehydes or ketones of formula (II) over time. Furthermore, as a side reaction, the compounds according to formula (I), in particular if X is of formula (i), are able to generate thiols of formula (II'). In formulae (II) and (II') each $R^{1(')}$ represents either $R^1$ or $R^{1'}$, $R^{2(')}$ represents either $R^2$ or $R^{2'}$ and $R^{3(')}$ represents either $R^3$ or $R^{3'}$ all having the same meaning as indicated in formula (I), and with the proviso that within the same molecule of (II) or (II') all $R^{1(')}$, $R^{2(')}$ and $R^{3(')}$ represent either $R^1$, $R^2$ or $R^3$, or $R^{1'}$, $R^{2'}$ or $R^{3'}$.

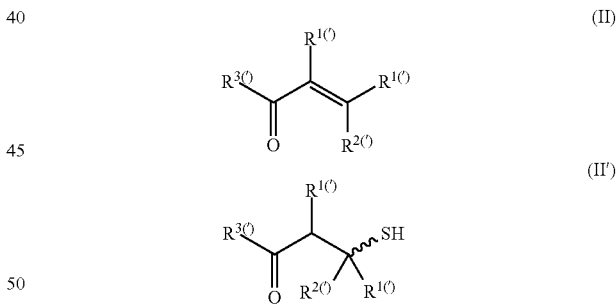

The compounds of formula (I) are non-volatile and essentially odorless. At the same time they are relatively stable in perfuming compositions or perfumed articles. When exposed to a surface under environmental conditions compounds (II) and/or (II') are believed to be formed by reaction with ambient humidity. The generation of these compounds may further be triggered by the presence of oxygen in the air, by pH changes, by exposure to light, in particular to UV-A light, the presence of enzymes, or at increased temperature, or by other types of mechanisms, or by the combination of several mechanisms.

Non-volatile and essentially odorless compounds are advantageously characterized by a vapor pressure below 2.0 Pa, as obtained by calculation using the software EPIwin v. 3.10 (2000, available at the US Environmental Protection Agency). Preferably, said vapor pressure is below 0.2 Pa, or even more preferably below 0.02 Pa.

Although it is not possible to provide an exhaustive list of the compounds of formula (II) or (II') which are generated from the invention's compound of formula (I), one can cite as preferred and non-limiting examples the following: 1-(2,6,6-trimethylcyclohex-2-en-1-yl)but-2-en-1-one (alpha-damascone), 1-(2,6,6-trimethylcyclohex-1-en-1-yl)but-2-en-1-one (beta-damascone), 1-(2,2-dimethyl-6-methylenecyclohexyl)but-2-en-1-one (gamma-damascone), 1-(2,6,6-trimethylcyclohex-3-en-1-yl)but-2-en-1-one (delta-damascone), 1-(6-ethyl-2,6-dimethylcyclohex-3-en-1-yl)2-buten-1-one, 2-methyl-1-(2,6,6-trimethylcyclohex-2-en-1-yl)but-2-en-1-one, 2-methyl-1-(2,6,6-trimethylcyclohex-1-en-1-yl)but-2-en-1-one, 1-(2,2-dimethyl-6-methylenecyclohexyl)-2-methylbut-2-en-1-one, 2-methyl-1-(2,6,6-trimethylcyclohex-3-en-1-yl)but-2-en-1-one, 4-(2,6,6-trimethylcyclohex-2-en-1-yl)but-3-en-2-one (alpha-ionone), 4-(2,6,6-trimethylcyclohex-1-en-1-yl)but-3-en-2-one (beta-ionone), 4-(2,2-dimethyl-6-methylenecyclohexyl)but-3-en-2-one (gamma-ionone), 4-(2,6,6-trimethylcyclohex-3-en-1-yl)but-3-en-2-one (delta-ionone), 1-(2,6,6-trimethylcyclohexa-1,3-dien-1-yl)but-2-en-1-one, 1-(2,2,3,6-tetramethylcyclohexyl)but-2-en-1-one, 4-(2,2,3,6-tetramethylcyclohexyl)but-3-en-2-one, 1-(5,5-dimethyl-cyclohex-1-en-1-yl) pent-4-en-1-one, 3-methyl-5-propyl-2-cyclohexen-1-one, 3-mercapto-3-methyl-5-propylcyclohexan-1-one, 3-methylcyclohex-2-en-1-one, 3-mercapto-3-methylcyclohexan-1-one, 3-methylcyclopent-2-en-1-one, 3-mercapto-3-methylcyclopentan-1-one, 2-methyl-5-(prop-1-en-2-yl)cyclohex-2-en-1-one (carvone), 5-methyl-2-(propan-2-ylidene)cyclohexan-1-one (pulegone), 2-(2-mercaptopropan-2-yl)-5-methylcyclohexan-1-one, 1-(3,3-dimethyl-1-cyclohexen-1-yl)-4-penten-1-one, 1-(5-ethyl-5-methylcyclohex-1-en-1-yl)pent-4-en-1-one, 3,7-dimethylocta-2,6-dienal (citral), oct-2-en-4-one, 2-mercaptooctan-4-one, 5-methylhex-4-en-3-one, 5-mercapto-5-methylhexan-3-one, 4-methylpent-3-en-2-one, 4-mercapto-4-methylpentan-2-one, 3-methylpent-3-en-2-one, 4-mercapto-3-methylpentan-2-one, 3-methylbut-2-enal, 3-mercapto-3-methylbutanal, but-2-enal or 3-mercaptobutanal and/or mixtures thereof.

The compounds of formula (I) with X being of formula (i) may be synthesized by 1,4-addition reaction of a compound of formula HX-Q-XH with an α,β-unsaturated aldehyde or ketone of formula (II), wherein all the symbols have the meaning as indicated in formula (I). Compounds of formula (I) with X being structures (ii) or (iii) can then be obtained in a second step by (partial) oxidation from compounds of formula (I) with X being of formula (i).

Compounds of formula (I) can be prepared using either one single or two different α,β-unsaturated aldehydes or ketones of formula (II). If two different α,β-unsaturated aldehydes or ketones are used, compounds of formula (I) with different $R^1$, $R^2$, $R^3$ and $R^{1'}$, $R^{2'}$, $R^{3'}$ groups are obtained. Preferably only one α,β-unsaturated aldehyde or ketone of formula (II) is reacted with a compound of formula HX-Q-XH.

Compounds of formula (I) with X being of formula (i) can be synthesized from one molar equivalent of a compound of formula HX-Q-XH and two molar equivalents of one or several α,β-unsaturated aldehydes or ketones of formula (II). Alternatively, compounds of formula (I) can be synthesized from one molar equivalent of a compound of formula HX-Q-XH and less than two molar equivalents of one or several α,β-unsaturated aldehydes or ketones of formula (II). Preferably, compounds of formula (I) are synthesized using a slight molar excess of one or several α,β-unsaturated aldehydes or ketones of formula (II) with respect to the compound of formula HX-Q-XH. Preferably, 2.5 molar equivalents or more of one or several α,β-unsaturated aldehydes or ketones of formula (II) are used with respect to the compound of formula HX-Q-XH, even more preferably 2.2 molar equivalents are used, most preferably 2.1 molar equivalents are used. The final compound of formula (I) may thus contain some remaining compound(s) of formula (II).

Compounds of formula (I) with X being of formula (i) may optionally be synthesized from a compound of formula HS-Q-SH and one or several α,β-unsaturated aldehydes or ketones of formula (II) in the presence of a base, which is acting as a catalyst. Preferably, the base used for the transformation is 1,8-diazabicyclo[5.4.0]undec-7-ene (DBU). The reaction can be carried out in the presence or in the absence of a solvent.

Compounds of formula (I) with X being of formula (ii) or (iii) are preferably prepared by oxidation of the corresponding compound of formula (I) with X being of formula (i). For the preparation of compounds of formula (I) with X being of formula (ii), Oxone (2 $KHSO_5/KHSO_4/K_2SO_4$) might be used as the oxidizing agent.

Although it is not possible to provide an exhaustive list of the compounds of formula HX-Q-XH which may be used in the synthesis of the invention's compounds, one can cite as preferred and non-limiting examples the following: 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,5-dimercapto-3-oxapentane, 1,8-dimercapto-3,6-dioxaoctane, 1,11-dimercapto-3,6,9-trioxaundecane or 1,14-dimercapto-3,6,9,12-tetraoxatetradecane.

Although it is not possible to provide an exhaustive list of the compounds of formula (II) which may be used in the synthesis of the invention's compounds, one can cite as preferred and non-limiting examples the following: 1-(2,6,6-trimethylcyclohex-2-en-1-yl)but-2-en-1-one (alpha-damascone), 1-(2,6,6-trimethylcyclohex-1-en-1-yl)but-2-en-1-one (beta-damascone), 1-(2,2-dimethyl-6-methylenecyclohexyl)but-2-en-1-one (gamma-damascone), 1-(2,6,6-trimethylcyclohex-3-en-1-yl)but-2-en-1-one (delta-damascone), 1-(6-ethyl-2,6-dimethylcyclohex-3-en-1-yl)2-buten-1-one, 2-methyl-1-(2,6,6-trimethylcyclohex-2-en-1-yl)but-2-en-1-one, 2-methyl-1-(2,6,6-trimethylcyclohex-1-en-1-yl)but-2-en-1-one, 1-(2,2-dimethyl-6-methylenecyclohexyl)-2-methylbut-2-en-1-one, 2-methyl-1-(2,6,6-trimethylcyclohex-3-en-1-yl)but-2-en-1-one, 3-methyl-4-(2,6,6-trimethyl-2-cyclohexen-1-yl)-3-buten-2-one, 1-(2,6,6-trimethyl-2-cyclohexen-1-yl)-1-penten-3-one, 4-(2,6,6-trimethylcyclohex-2-en-1-yl)but-3-en-2-one (alpha-ionone), 4-(2,6,6-trimethylcyclohex-1-en-1-yl)but-3-en-2-one (beta-ionone), 4-(2,2-dimethyl-6-methylenecyclohexyl)but-3-en-2-one (gamma-ionone), 4-(2,6,6-trimethylcyclohex-3-en-1-yl)but-3-en-2-one (delta-ionone), 1-(2,6,6-trimethylcyclohexa-1,3-dien-1-yl)but-2-en-1-one, 1-(2,2,3,6-tetramethylcyclohexyl)but-2-en-1-one, 4-(2,2,3,6-tetramethylcyclohexyl)but-3-en-2-one, 1-(3,3- and 5,5-dimethylcyclohex-1-en-1-yl) pent-4-en-1-one, 3-methyl-5-propyl-2-cyclohexen-1-one, 3-methylcyclohex-2-en-1-one, 3-methylcyclopent-2-en-1-one, 2-methyl-5-(prop-1-en-2-yl) cyclohex-2-en-1-one (carvone), 5-methyl-2-(propan-2-ylidene)cyclohexan-1-one (pulegone), 1-(3,3-dimethyl-1-cyclohexen-1-yl)-4-penten-1-one, 1-(5-ethyl-5-methylcyclohex-1-en-1-yl)pent-4-en-1-one, 3,7-dimethylocta-2,6-dienal (citral), oct-2-en-4-one, 5-methylhex-4-en-3-one, 4-methylpent-3-en-2-one, 3-methylpent-3-en-2-one, 3-methylbut-2-enal or but-2-enal.

α,β-Unsaturated aldehydes or ketones of formula (II) generated from the compounds of formula (I) or used for the synthesis of compounds of formula (I) can be in the (E) form, or in the (Z) form, or in mixtures thereof.

The compounds of formula (I) can be obtained and used as a mixture of several different compounds of formula (I) and/or as a mixture with one or several compounds of formula (II), or be further purified according to standard methods known to expert in the field.

Mixtures of compounds (I) and (II) comprise at least 70% of compound (I), preferably more than 80% of compound (I), even more preferably more than 90% of compound (I), and most preferably more than 95% of compound (I).

The compounds of formula (I) can also be obtained and used in a mixture with a compound of formula

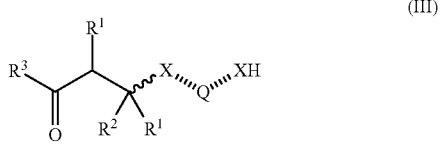

(III)

which is also part of the present invention, and wherein all the symbols have the same meaning as indicated in formula (I).

Mixtures of compounds (I) and (III) comprise at least 30% of compound (I), preferably more than 50% of compound (I), even more preferably more than 75% of compound (I), even more preferably more than 90% of compound (I), and most preferably more than 95% of compound (I).

As mentioned above, the invention concerns the use of a compound of formula (I) as perfuming ingredient to provide a long-lasting odor, in particular a floral and fruity odor, to the environment. In other words, it concerns a method to confer, enhance, improve or modify the odor, in particular floral and fruity odor, of a perfuming composition or of a perfumed article, which method comprises adding to said composition or article an effective amount of at least a compound of formula (I). By "use of a compound of formula (I)" it has to be understood here also the use of any composition containing a compound of formula (I) and which can be advantageously employed in the perfumery industry.

By "perfuming ingredient" it is meant here a compound, which is used in a perfuming preparation or a composition to impart a hedonic effect. In other words such perfuming ingredient, to be considered as being a perfuming one, must be recognized by a person skilled in the art as being able to impart or modify in a positive or pleasant way the odor of a composition, and not just as having an odor.

The expression "floral and fruity odor" or "floral and fruity note" should be understood as an odor reminding that of a floral, e.g. rosy, and fruity olfactive impression, in particular red berry notes, such as for example raspberry or strawberry notes, fruity-floral notes such as cassis, blackcurrant and exotic fruit notes. "Fresh" odors can be associated with fruity and floral, but also with citrus and green tonalities, with "green" odors reminding e.g the odor of freshly cut grass. "Fresh green" odors can also have herbaceous and minty tonalities.

For sake of clarity, a long-lasting effect is typically achieved if, after a certain time, e.g. after several hours or days, a given compound emits higher amounts of an odor into the environment than a reference compound providing the same type of odor. Thus, the expression "long-lasting floral and fruity notes" when referring to the compound of formula (I) of the invention should be understood as an increase of duration of the floral and fruity odor perception (release of compounds in the atmosphere providing a floral and fruity olfactive impression) as compared to the one of the molecules having such an impression alone, and measured under the same conditions for example after several hours (6 or 8 hours) or days (1 or 3 days).

Said compositions, which in fact can be advantageously employed as perfuming ingredients, are also an object of the present invention.

Therefore, another aspect of the present invention is a perfuming composition comprising:
  i) as perfuming ingredient, at least one invention's compound as defined above;
  ii) at least one ingredient selected from the group consisting of a perfumery carrier and a perfumery base; and
  iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluril, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Other resins are those produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine-based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such coreshell microcapsules following prior art methods that are also further detailed and exemplified in the patent literature. U.S. Pat. No. 4,396,670, to the Wiggins Teape Group Limited, is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-8054.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition in addition to the perfuming ingredient of formula (I), and imparting such as the perfuming ingredient of formula (I) a hedonic effect. In other words, such a co-ingredient, to be considered as being a perfuming one, must be recognized by a person skilled in the art as being able to impart or modify in a positive or pleasant way the odor of a composition, and not just as having an odor.

In particular, perfuming co-ingredients that might be used in a perfuming preparation or a composition according to the invention include as non-limiting examples:

a) natural or nature-identical ingredients and natural extracts, preferably those obtained from red berries, such as strawberries or raspberries;

b) ingredients with strawberry notes, such as oct-2-en-4-one, 2,5-dimethyl-4-hydroxy-2H-furan-3-one (Furaneol®), 5-ethyl-4-hydroxy-2-methyl-3(2H)-furanone, 2,5-dimethyl-4-oxo-4,5-dihydrofuran-3-yl acetate, ethyl 3-methyl-3-phenyloxirane-2-carboxylate (Strawberry Pure®), ethyl 3-phenyloxirane-2-carboxylate, methyl 2-acetamidobenzoate or 3-phenylpropyl 3-methylbutanoate, 2-methyl-4-oxo-4H-pyran-3-yl propionate, 2-methylpent-2-enoic acid or (2S,5S)-2-(tert-butyl)-5-methyl-2-propyltetrahydrofuran (Dihydrocassyrane®);

c) ingredients with raspberry notes, such as 4-(4-methoxyphenyl)butan-2-one (raspberry ketone);

d) ingredients with other fruity notes, such as ethyl butyrate, ethyl 2-methylbutanoate, ethyl 2-methyl-pentanoate, gamma-nonalactone, gamma-undecalactone, hexyl acetate, allyl heptanoate, allyl 3-cyclohexylpropanoate, 2-phenoxyethyl isobutyrate, 2,2,5-trimethyl-5-pentylcyclopentanone, 2-methyl-4-propyl-1,3-oxathiane, 4-decanolide, 5-heptyldihydrofuran-2(3H)-one, 3-methyl-2-hexen-1-yl acetate, 1-(3,3-dimethylcyclohexyl)ethyl(3-ethyl-2-oxiranyl)acetate, ethyl 2-(2-methyl-1,3-dioxolan-2-yl)acetate (Fructone®) or diethyl cyclohexane-1,4-dicarboxylate (Fructalate®);

e) ingredients with caramel notes, such as 2-ethyl-3-hydroxy-4H-pyran-4-one;

f) ingredients with citrus notes, such as 1-methyl-4-(1-methylethenyl)-cyclohexene (Limonene), 2,6-dimethyl-7-octen-2-ol (dihydromyrcenol), 1,5-dimethyl-1-vinyl-4-hexenyl acetate (linalyl acetate), 3,7-dimethyl-6-octenenitrile, 1-p-menthen-8-yl acetate or 1,4(8)-p-menthadiene;

g) ingredients with flowery citrus notes, such as methyl 2-(3-oxo-2-pentylcyclopentyl)acetate (Hedione®);

h) ingredients with flowery notes, such as 3,7-dimethylocta-1,6-dien-3-ol (Linalool), 3,7-dimethyl-3-octanol, 3,7-dimethyl-6-octen-1-ol (citronellol), 3,7-dimethyl-2,6-octadien-1-ol (geraniol, nerol), 2-phenylethanol, 3-methylbutyl 2-hydroxybenzoate, pentyl 2-hydroxybenzoate, 1-(6-ethyl-2,6-dimethylcyclohex-3-en-1-yl) 2-buten-1-one, hexyl 2-hydroxybenzoate, benzyl 2-hydroxybenzoate or cyclohexyl 2-hydroxybenzoate, 3-(4-tert-butylphenyl)-2-methylpropanal, 2-pentyl-3-phenyl-2-propenal, 2-hexyl-3-phenyl-2-propenal, benzyl acetate, tetrahydro-2-isobutyl-4-methyl-4(2H)-pyranol, methyl 2-(methylamino)benzoate, 2,5-dimethyl-2-indanmethanol, 2,6,6-trimethyl-3-cyclohexene-1-carboxylate, 3-(4,4-dimethyl-1-cyclohexen-1-yl)

propanal, 3,7-dimethyl-1,6-nonadien-3-ol, 3-(4-isopropylphenyl)-2-methylpropanal, tricyclo[5.2.1.0(2,6)]dec-3- and 4-en-8-yl acetate, tricyclo[5.2.1.0(2,6)]dec-3- and 4-en-8-yl propionate, tricyclo[5.2.1.0(2,6)]dec-3- and 4-en-8-yl 2-methylpropanoate, p-menth-1-en-8-ol, 4-(1,1-dimethylethyl)-1-cyclohexyle acetate, 1,1-dimethyl-2-phenylethyl acetate, 3,7-dimethyl-2,6-octadienyl acetate, 7-methyloctyl acetate, 4-(1,1-dimethylethyl)-1-cyclohexyl acetate, 4-cyclohexyl-2-methyl-2-butanol, 3-methyl-5-phenyl-1-pentanol, cis-7-p-menthanol, propyl(S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, 8-decen-5-olide or 4-phenyl-2-butanone;

i) ingredients with flowery woody notes, such as 1-(octahydro-2,3,8,8-tetrame-2-naphthalenyl)-1-ethanone (Iso E Super®, mixture of isomers);

j) ingredients with green notes, such as (Z)-hex-3-en-1-ol, (Z)-hex-3-en-1-yl acetate, (Z)-hex-3-en-1-yl butyrate, (Z)-hex-3-en-1-yl benzoate, (Z)-hex-3-en-1-yl 2-hydroxybenzoate, 2-methyl-3-hexanone (E)-oxime, 2,4-dimethyl-3-cyclohexene-1-carbaldehyde, 2-tert-butyl-1-cyclohexyl acetate, 1-phenylethyl acetate, allyl(2-methylbutoxy)acetate, 4-methyl-3-decen-5-ol or diphenyl ether;

k) ingredients with musky notes, such as 1,4-dioxa-5,17-cycloheptadecanedione, (Z)-4-cyclopentadecen-1-one, (9Z)-9-cycloheptadecen-1-one, 2-{1S)-1-[(1R)-3,3-dimethylcyclohexyl]ethoxy}-2-oxoethyl propionate 3-methyl-5-cyclopentadecen-1-one, [1-(3',3'-dimethyl-1'-cyclohexyl)ethoxycarbonyl]methyl propanoate, 1,3,4,6,7,8-hexahydro-4,6,6,7,8,8-hexamethyl-cyclopenta-g-2-benzopyrane, oxacyclohexadecan-2-one (Exaltolide®), oxacyclohexadec-12- and/or 13-en-2-one (Habanolide®), 3-methylcyclopentadecan-1-one (Muscone®), (Z)-3-methylcyclopentadec-5-en-1-one (Muscenone®) or 2-(1-(3,3-dimethylcyclohexyl)ethoxy)-2-methylpropyl propionate (Helvetolide®).

In an alternative embodiment, the perfuming co-ingredients that might be used in a perfuming preparation or a composition according to the invention include as non-limiting examples 1-(2,6,6-trimethylcyclohex-2-en-1-yl)but-2-en-1-one (alpha-damascone), 1-(2,6,6-trimethylcyclohex-1-en-1-yl)but-2-en-1-one (beta-damascone), 1-(2,2-dimethyl-6-methylenecyclohexyl)but-2-en-1-one (gamma-damascone), 1-(2,6,6-trimethylcyclohex-3-en-1-yl)but-2-en-1-one (delta-damascone), 2-methyl-1-(2,6,6-trimethylcyclohex-2-en-1-yl)but-2-en-1-one, 2-methyl-1-(2,6,6-trimethylcyclohex-1-en-1-yl)but-2-en-1-one, 1-(2,2-dimethyl-6-methylenecyclohexyl)-2-methylbut-2-en-1-one, 2-methyl-1-(2,6,6-trimethylcyclohex-3-en-1-yl)but-2-en-1-one, 3-methyl-4-(2,6,6-trimethyl-2-cyclohexen-1-yl)-3-buten-2-one, 1-(2,6,6-trimethyl-2-cyclohexen-1-yl)-1-penten-3-one, 4-(2,6,6-trimethylcyclohex-2-en-1-yl)but-3-en-2-one (alpha-ionone), 4-(2,6,6-trimethylcyclohex-1-en-1-yl)but-3-en-2-one (beta-ionone), 4-(2,2-dimethyl-6-methylenecyclohexyl)but-3-en-2-one (gamma-ionone), 4-(2,6,6-trimethylcyclohex-3-en-1-yl)but-3-en-2-one (delta-ionone), 1-(2,6,6-trimethylcyclohexa-1,3-dien-1-yl)but-2-en-1-one, 1-(2,2,3,6-tetramethylcyclohexyl)but-2-en-1-one, 4-(2,2,3,6-tetramethylcyclohexyl)but-3-en-2-one, 1-(3,3- and 5,5-dimethylcyclohex-1-en-1-yl) pent-4-en-1-one, 3-methyl-5-propyl-2-cyclohexen-1-one, 3-mercapto-3-methyl-5-propylcyclohexan-1-one, 3-methylcyclohex-2-en-1-one, 3-mercapto-3-methylcyclohexan-1-one, 3-methylcyclopent-2-en-1-one, 3-mercapto-3-methylcyclopentan-1-one, 2-methyl-5-(prop-1-en-2-yl)cyclohex-2-en-1-one (carvone), 5-methyl-2-(propan-2-ylidene)cyclohexan-1-one (pulegone), 2-(2-mercaptopropan-2-yl)-5-methylcyclohexan-1-one, 1-(3,3-dimethyl-1-cyclohexen-1-yl)-4-penten-1-one, 1-(5-ethyl-5-methylcyclohex-1-en-1-yl)pent-4-en-1-one, 3,7-dimethylocta-2,6-dienal (citral), oct-2-en-4-one, 2-mercaptooctan-4-one, 5-methylhex-4-en-3-one, 5-mercapto-5-methylhexan-3-one, 4-methylpent-3-en-2-one, 4-mercapto-4-methylpentan-2-one, 3-methylpent-3-en-2-one, 4-mercapto-3-methylpentan-2-one, 3-methylbut-2-enal, 3-mercapto-3-methylbutanal, but-2-enal or 3-mercaptobutanal.

Furthermore, the person skilled in the art is able to select other perfuming co-ingredients on the basis of the general knowledge and according to the intended use or application and the desired organoleptic effect to be achieved. The nature and type of these other perfuming co-ingredients do not warrant a more detailed description here, which in any case would not be exhaustive. In general terms, these perfuming co-ingredients belong to chemical classes as varied as alcohols, lactones, aldehydes, ketones, esters, ethers, acetates, nitriles, terpenoids, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds, or can be an encapsulated perfume.

The term "perfumery adjuvant" is understood as an ingredient capable of imparting additional added benefit such as a color, a particular light resistance, chemical stability etc. A detailed description of the nature and type of adjuvant commonly used in perfuming bases cannot be exhaustive, but it has to be mentioned that the ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants, heat/light and or buffers or chelating agents, such as BHT), coloring agents (e.g. dyes and/or pigments), preservatives (e.g. antibacterial or antimicrobial or antifungal or anti-irritant agents), abrasives, skin cooling agents, fixatives, insect repellants, ointments, vitamins and mixture thereof.

It is understood that a person skilled in the art is perfectly able to design optimal formulations for the desired effect by admixing the above-mentioned components of a perfuming composition, simply by applying the standard knowledge of the art as well as by trial and error methodologies.

Other suitable perfumery adjuvants optionally used in combination with the compounds according to the present invention comprise tertiary amines, in particular those with high water solubility, such as triethanolamine, methyldiethanolamine, dimethylethanolamine, alkyldiethanolamines and ethoxylated alkyldiethanolamines.

A particular aspect of the invention's perfumery compositions concerns the ones further optionally comprising (in addition to the above-mentioned compositions) at least one compound selected amongst the isothiazolones of formula

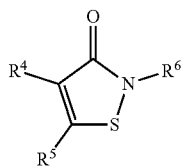

(IV)

wherein
- $R^4$ and $R^5$ represent, separately and independently of each other, a hydrogen atom, a halogen atom, preferably chlorine, a $C_1$-$C_4$ linear or branched alkyl group, an amino group or a benzylamino group; or, alternatively, $R^4$ and $R^5$ are taken together to represent a phenyl or pyridine ring, possibly substituted with one to four $C_1$-$C_4$ linear or branched alkyl or alkenyl groups and/or one to two halogen atoms, preferably chlorine atoms; and
- $R^6$ represents a hydrogen atom, an alkali metal atom, in particular Na or K, a phenyl or benzyl group possibly substituted with one or two halogen atoms and/or one or two methyl, trifluoromethyl, methoxy or amino groups, an amine group, or a $C_1$-$C_8$ unsaturated, linear, branched or cyclic hydrocarbon group possibly substituted with one or two nitrogen, oxygen or halogen atoms.

According to a particular embodiment of the invention said compound of formula (IV) is one wherein $R^4$ and $R^5$ represent, separately and independently of each other, a hydrogen atom, a chlorine atom or a methyl group or, alternatively, $R^4$ and $R^5$ are taken together to represent a phenyl ring, and $R^6$ represents a hydrogen atom or a methyl group.

According to a particular embodiment of the invention, said compound of formula (IV) is selected from the group of isothiazolones consisting of 1,2-benzisothiazol-3(2H)-one, 4- or 5-chloro-2-methylisothiazol-3(2H)-one or 2-methylisothiazol-3(2H)-one, or more preferably 5-chloro-2-methylisothiazol-3(2H)-one or 1,2-benzisothiazol-3(2H)-one, and most preferably 1,2-benzisothiazol-3(2H)-one.

According to a particular embodiment of the invention, said compound of formula (IV) is present in the compositions of the invention at a weight concentration of 0.0% to 5%, relative to the total weight of the composition. According to more preferred embodiments of the invention, the concentration of compound of formula (IV) is comprised between 0.001 and 3% of the total weight, preferably between 0.005 and 0.1%.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that is important to have the possibility, in the compositions mentioned above, to use in addition to a compound of formula (I) other compounds of similar or different nature being able to generate other fragrances, as it enables the perfumer to prepare accords, perfumes, possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as the mixture does not provide the inventive compound in a suitable form for perfumery. Thus, unpurified reaction mixtures are generally excluded from the present invention unless otherwise specified.

Furthermore, the invention's compound of formula (I) can also be advantageously used in all the fields of modern perfumery, i.e. fine or functional perfumery, to positively impart a long-lasting or substantive strawberry odor to a consumer product into which said compound (I) is added.

Consequently, another aspect of the present invention relates to a perfuming consumer product comprising as perfuming ingredient, at least one compound of formula (I) or a perfuming composition, as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfumed consumer product according to the invention is a perfumed consumer product which comprises the functional formulation, as well as optionally additional benefit agents, corresponding to the desired consumer product, e.g. a conditioner, a detergent or an air freshener, and an olfactively effective amount of at least one invention's compound. For the sake of clarity, the perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of the product.

As used herein "consumer product" means baby care, personal care, fabric & home care, family care, feminine care, health care, beauty care and like products generally intended to be used or consumed in the form in which they are sold.

Non-limiting examples of suitable perfuming consumer product can be a perfume, such as a fine perfume, a cologne or an after-shave lotion; a fabric care product, such as a liquid or solid detergent or a unidose detergent (like a powder tablet, a liquid unidose or a multichamber unidose detergent), a fabric softener, a fabric refresher, an ironing water, a paper, a bleach, a carpet cleaner, or curtain-care product; a body-care product, such as a hair care product (e.g. a shampoo, a coloring preparation or a hair spray, a color care product or a hair shaping product), a dental care product, a disinfectant, an intimate care product), a cosmetic preparation (e.g. a skin cream or lotion, a vanishing cream or a deodorant or antiperspirant (e.g. a spray or roll on), a hair remover, a tanning, sun or after sun product, a nail product, a skin cleansing product or a makeup), a skin-care product (e.g. a perfumed soap, shower or bath mousse, oil or gel, a hygiene product or a foot/hand care product); an air care product, such as an air freshener or a "ready to use" powdered air freshener, which can be used in the home space (rooms, refrigerators, cupboards, shoes or car) and/or in a public space (halls, hotels, malls, etc.); or a home care product, such as a mold remover, a furnisher care product, a wipe, a dish detergent or hard-surface (e.g. a floor, bath, sanitary or a windows) detergent, a leather care product; a car care product, such as a polish, waxes or a plastic cleaner.

Preferred perfuming compositions or perfumed articles are perfumes, fabric or hard-surface detergents, hair-care products and fabric softeners or refreshers.

Typical examples of fabric detergents or softener compositions into which the compounds of the invention can be incorporated are described in WO 97/34986, or in U.S. Pat. Nos. 4,137,180 and 5,236,615 or in EP 799 885. Other typical detergents and softening compositions which can be used are described in works such as Ullmann's Encyclopedia of Industrial Chemistry, vol. 20, Wiley-VCH, Weinheim, p. 355-540 (2012); Flick, Advanced Cleaning Product Formulations, Noye Publication, Park Ridge, New Jersey (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat, oxidation or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 2 or 5% by weight, can be used when these compounds are incorporated into perfumed articles, percentage being relative to the weight of the article.

As mentioned above, the invention concerns a method of imparting a long-lasting or substantive floral and fruity odor to surfaces, such as hard surfaces, fabric, skin or hair. Perfume ingredients that provide a floral and fruity odor to the environment by evaporation from a surface are typically not very long-lasting or substantive. As outlined above, one reason for this is their relatively high volatility, which guarantees an efficient evaporation after surface deposition. Another reason for this is that quite often only small amounts of these compounds are efficiently deposited on the surface. This is in particular the case if they are applied to a surface via perfuming compositions or perfumed articles, which are rinsed after application. This rinsing step also carries away a large amount of the perfume, which is supposed to remain on the target surface. Examples for this case are washing and cleaning agents, such as hard surface cleaners, detergents, shower gels shampoos and the like, which are rinsed off after application. Furthermore, perfuming a surface by bringing it into contact with perfuming compositions or perfumed articles from which the perfume is deposited onto the surface by a partition equilibrium between the perfuming compositions or perfumed articles and the corresponding surface might be inefficient for the deposition of the perfume. Examples for this case are conditioners or surface refreshers, such as fragrance softeners, which are brought into contact with the target and then removed or left drying. Compounds of formula (I) according to the present invention are suitable to enhance the deposition of the perfume and thus to impart a long-lasting floral and fruity odor to surfaces, such as hard surfaces, fabric, skin or hair.

Therefore, another aspect of the present invention concerns a method of imparting a long-lasting or substantive fruity and floral odor to surfaces, such as hard surfaces, fabric, skin or hair, by adding at least one compound of formula (I) to perfuming compositions or perfumed articles and applying them to the corresponding targeted surface.

The present invention also relates to a microcapsule comprising at least one compound of formula (I). In one embodiment, the at least one compound of formula (I) is encapsulated in a core-shell microcapsule wherein the at least one compound of formula (I) is contained in the core surrounded by the shell. In one embodiment, the shell of the microcapsule protects the compound of formula (I) from the environment. The shell is made of material which is able to release the at least one compound of formula (I). In one embodiment, the shell is made of material which is able to release the compound of formula (I) upon breakage of the shell and/or by diffusion through the shell. A person skilled in the art is well aware of processes to prepare said microcapsules.

The nature of the polymeric shell from the microcapsules of the invention can vary. As non-limiting examples, the shell can be aminoplast-based, polyamide-based, polyester-based, polyurea-based or polyurethane-based.

According to an embodiment, the shell is a biopolymer-based shell comprising a protein.

The shell can also be a hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast co-polymer, such as melamine-formaldehyde or urea-formaldehyde or cross-linked melamine formaldehyde or melamine glyoxal.

According to another embodiment, the microcapsules have a polymeric shell resulting from complex coacervation wherein the shell is possibly cross-linked.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerization between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine is optional.

According to a particular embodiment, the colloidal stabilizer includes an aqueous solution of between 0.1% and 0.4% of polyvinyl alcohol, between 0.6% and 1% of a cationic co-polymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and/or mixtures thereof.

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Missouri U.S.A.), Cytec Industries (West Paterson, New Jersey U.S.A.), Sigma-Aldrich (St. Louis, Missouri U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together a) a polyamine component in the form of melamine or of a mixture of melamine and at least one $C_1$-$C_4$ compound comprising two $NH_2$ functional groups;

b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and c) a protic acid catalyst;

2) preparing an oil-in-water dispersion, wherein the droplet size is comprised between 1 and 600 μm, and comprising:
   i. an oil;
   ii. a water medium
   iii. at least an oligomeric composition as obtained in step 1;
   iv. at least a cross-linker selected amongst
      A) $C_4$-$C_{12}$ aromatic or aliphatic di- or tri-isocyanates and their biurets, triurets, trimers, trimethylol propane-adduct and mixtures thereof; and/or
      B) a di- or tri-oxiran compound of formula Q-(oxiran-2-ylmethyl)$_n$
         wherein n stands for 2 or 3 and Q represents a $C_2$-$C_6$ group optionally comprising from 2 to 6 nitrogen and/or oxygen atoms;
      v. optionally a $C_1$-$C_4$ compound comprising two $NH_2$ functional groups;

3) Heating said dispersion;
4) Cooling said dispersion.

This process is described in more details in WO 2013/068255, the content of which is included by reference.

According to another embodiment, the shell of the microcapsule is polyurea- or polyurethane-based. Examples of processes for the preparation of polyurea and polyureathane-based microcapsule slurry are for instance described in WO 2007/004166, EP 2300146, EP 2579976 the contents of which are also included by reference. Typically a process for the preparation of polyurea or polyurethane-based microcapsule slurries include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and 50 μm;
d) Applying conditions sufficient to induce interfacial polymerisation and form microcapsules in the form of a slurry.

In an alternative embodiment, the capsule may be a granule wherein the hydrophobic ingredient; i.e. the invention's polymer, is dispersed or adsorbed in a matrix or a carrier being a water soluble material.

According to any embodiment, the water soluble matrix or carrier is a monomeric, oligomeric or polymeric carrier material, or a mixture of two or more of these. An oligomeric carrier is a carrier wherein 2-10 monomeric units are linked by covalent bonds. For example, if the oligomeric carrier is a carbohydrate, the oligomeric carrier may be sucrose, lactose, raffinose, maltose, trehalose, or a fructo-oligosaccharide.

Examples of monomeric carrier materials are glucose, fructose, mannose, galactose, arabinose, fucose, sorbitol, mannitol.

Polymeric carriers have more than 10 monomeric units that are linked by covalent bonds.

The carrier may be a polymeric carrier material. Non-limiting examples of polymeric carrier materials include urea, polyvinyl acetates, polyvinyl alcohol, dextrins, maltodextrins, glucose syrups, natural or modified starch, polysaccharides, carbohydrates, chitosan, gum Arabic, polyethylene glycol (PEG), polyvinyl pyrrolidone, acrylamides, acrylates, methacrylates, polyacrylic acid and related structures, maleic anhydride co-polymers, amine-functional polymers, polyvinyl benzyl chloride, vinyl ethers, styrenes, polystyrenesulfonates, vinyl acids, ethylene glycol-propylene glycol block co-polymers, vegetable gums, gum acacia, pectins, xanthanes, alginates, carragenans, cellulose or cellulose derivatives, such as carboxymethyl methylcellulose, methylcellulose, ethylcellulose, propylcellulose or hydroxyethyl cellulose, polyols/sugar alcohols such as sorbitol, maltitol, xylitol, erythritol, and isomalt, PVP, citric acid or any water soluble solid acid, fatty alcohols or fatty acids and mixtures thereof.

According to a particular embodiment, the water soluble polymer comprises maltodextrin having a Dextrose Equivalent (DE) comprised between 3 and 20, preferably between 10 and 18.

According to an embodiment, the water soluble polymer comprises Maltodextrin 18DE and/or Maltodextrin 10DE.

According to a particular embodiment, the water soluble polymer comprises Maltodextrin 10DE.

According to an embodiment, the carrier is an inorganic material chosen in the group consisting of sodium chloride, sodium sulfate, sodium acetate, zeolite, sodium carbonate, sodium bicarbonate, clay, talc, calcium carbonate, magnesium sulfate, gypsum, calcium sulfate, magnesium oxide, zinc oxide, titanium dioxide, calcium chloride, potassium chloride, magnesium chloride, zinc chloride.

According to a particular embodiment, the solid carrier is sodium chloride and/or urea.

According to a particular embodiment, the solid carrier is sodium chloride.

According to a particular embodiment, the solid carrier is a mixture of clay and PEG, preferably the mixture comprises 0-30% of clay and 20-80% of PEG, preferably between 1-30% of clay and 20-80% of PEG, based on the total weight of the carrier.

According to a particular embodiment, the solid carrier is a mixture of sodium acetate and PEG, preferably the mixture comprises 0-80% of sodium acetate and 0-50% of PEG, preferably 1-80% of sodium acetate and 1-50% of PEG.

PEG has preferably a molecular weight greater than 1000 g/mol, preferably between 1000 and 8000 g/mol.

Examples of microcapsules suitable for use in the present invention include, but are not limited to the microcapsules disclosed in International Patent Application Publication No. WO 2007/026307 A2. Further examples include the microcapsules disclosed in International Patent Application Publication No. WO 2014/029695 A1. Additional examples include the microcapsules disclosed in International Patent Application Publication No. WO 2006/006003 A1. Additional examples include the microcapsules disclosed in International Patent Application Publication No. WO 2006/018964 A1. Additional examples include the microcapsules disclosed in International Patent Application Publication No. WO 2007/096790 A1. Additional examples include the microcapsules disclosed in International Patent Application Publication No. WO 2009/153695 A1. Additional examples include the microcapsules disclosed in European Patent No. EP 2379047.

Examples of methods to encapsulate the compound of formula (I) include, but are not limited to the microcapsules disclosed in International Patent Application Publication No. WO 2007/026307 A2. Further examples include the microcapsules disclosed in International Patent Application Publication No. WO 2014/029695 A1. Additional examples include the microcapsules disclosed in International Patent Application Publication No. WO 2006/006003 A1. Additional examples include the microcapsules disclosed in International Patent Application Publication No. WO 2006/018964 A1. Additional examples include the microcapsules disclosed in International Patent Application Publication No. WO 2007/096790 A1. Additional examples include the microcapsules disclosed in International Patent Application Publication No. WO 2009/153695 A1. Additional examples include the microcapsules disclosed in European Patent No. EP 2379047.

The compound of formula (I) may also release flavoring ingredients. So, a further aspect of the invention is a method to confer, enhance, improve or modify the flavor properties of a flavoring composition or of a flavored article, comprising adding to the composition or article an effective amount of at least one compound of formula (I) as defined above. A flavoring composition or a flavored consumer product comprising at least one compound of formula (I) is also part of the invention.

Examples

The invention is hereafter described in a more detailed manner by way of the following examples, wherein the abbreviations have the usual meaning in the art, temperatures are indicated in degrees centigrade (° C.). NMR spectral data were recorded on a Bruker AMX 500 spectrometer in CDCl$_3$ at 500 MHz for $^1$H and at 125.8 MHz for $^{13}$C if not indicated otherwise, the chemical displacements δ are indicated in ppm with respect to Si(CH$_3$)$_4$ as the standard, the coupling constants J are expressed in Hz (br.=broad peak). Reactions were carried out in standard glassware under N$_2$. Commercially available reagents and solvents were used without further purification if not stated otherwise.

Although specific conformations or configurations are indicated for some of the compounds, this is not meant to limit the use of these compounds to the isomers described. According to the invention, all possible conformation or configuration isomers are expected to have a similar effect.

Example 1

Preparation of Compounds According to Formula (I) and/or (III) Providing a Long-Lasting Floral and Fruity Odor (a) Synthesis of (±)-3,3'-(3,6-dioxaoctane-1,8-diyl-bis(sulfanediyl))bis(1-(2,6,6-trimethylcyclohex-3-en-1-yl)butan-1-one) (Compound 1), (±)-3,14-dimethyl-1-(2,6,6-trimethylcyclohex-3-en-1-yl)-7,10-dioxa-4,13-dithiaicosane-1,16-dione (Compound 2) and (±)-2,2'-(3,6-dioxaoctane-1,8-diylbis(sulfanediyl))bis(octan-4-one) (Compound 3)

(E)-trans-1-(2,6,6-trimethylcyclohex-3-en-1-yl)but-2-en-1-one (trans-delta-damascone, 2.00 g, 10.4 mmol), (E)-2-octen-4-one (1.30 g, 10.4 mmol) and 1,8-dimercapto-3,6-dioxaoctane (2.00 g, 8.4 mmol) were stirred at room temperature for 18 days. Column chromatography (SiO$_2$, n-heptane/ethyl acetate 9:1 to n-heptane/ethyl acetate 4:1), concentrating and drying under high vacuum for 1 h afforded 0.79 g (13%) of Compound 1, 0.64 g (12%) of Compound 2 and 0.64 g (14%) of Compound 3. The compounds were obtained as stereoisomeric mixtures. The three compounds can be used directly as a mixture, or can be used individually after separation.

$^1$H-NMR (Compound 1): 5.57-5.50 (m, 2 H), 5.49-5.41 (m, 2 H), 3.70-3.59 (m, 8 H), 3.39-3.29 (m, 2 H), 2.91 (dd, J=18.9, 4.8, 1 H), 2.81-2.66 (m, 6 H), 2.57-2.46 (m, 2 H), 2.53 (dd, J=18.6, 8.0, 1 H), 2.21 (dd, J=10.6, 6.7, 2 H), 2.01-1.91 (m, 2 H), 1.74-1.63 (m, 2 H), 1.31 and 1.30 (d, J=6.7, 6 H), 0.99, 0.97, 0.96 and 0.95 (s, 12 H), 0.89 (2 d, J=6.7, 6 H).

$^{13}$C-NMR (Compound 1): 212.31, 212.21, 131.82, 131.75, 124.25, 124.10, 71.00, 70.98, 70.31, 62.94, 62.83, 55.25, 55.17, 41.73, 41.72, 34.53, 34.51, 33.18, 33.06, 31.79, 31.56, 30.21, 30.14, 29.82, 29.79, 21.82, 21.63, 20.74, 20.73, 19.96, 19.88.

$^1$H-NMR (Compound 2): 5.57-5.50 (m, 1 H), 5.49-5.41 (m, 1 H), 3.71-3.58 (m, 8 H), 3.39-3.26 (m, 2 H), 2.91 (dd, J=18.6, 5.1, 0.5 H), 2.80-2.67 (m, 6 H), 2.57-2.47 (m, 2.5 H), 2.46-2.34 (m, 2 H), 2.21 (dd, J=10.6, 6.7, 1 H), 2.01-1.92 (m, 1 H), 1.74-1.66 (m, 1 H), 1.61-1.50 (m, 2 H), 1.36-1.24 (m, 2 H), 1.31 and 1.30 (d, J=6.7, 3 H), 1.28 (d, J=6.7, 3 H), 0.99, 0.97, 0.96 and 0.95 (s, 6 H), 0.91 (t, J=7.2, 3 H), 0.89 (2 d, J=6.7, 3 H).

$^{13}$C-NMR (Compound 2): 212.32, 212.21, 208.91, 131.81, 131.75, 124.26, 124.10, 71.02, 71.00, 70.98, 70.31, 62.95, 62.83, 55.25, 55.17, 50.06, 43.35, 41.73, 41.72, 35.38, 34.54, 34.51, 33.18, 33.06, 31.79, 31.57, 30.22, 30.14, 29.82, 29.79, 25.75, 22.30, 21.82, 21.76, 21.63, 20.74, 20.73, 19.96, 19.88, 13.86.

$^1$H-NMR (Compound 3): 3.68-3.59 (m, 8 H), 3.35-3.25 (m, 2 H), 2.77-2.67 (m, 6 H), 2.53 (dd, J=16.7, 8.0, 2 H), 2.47-2.34 (m, 4 H), 1.62-1.49 (m, 4 H), 1.37-1.25 (m, 4 H), 1.28 (d, J=6.7, 6 H), 0.91 (t, J=7.4, 6 H).

$^{13}$C-NMR (Compound 3): 208.92, 71.02, 70.31, 50.06, 43.34, 35.38, 30.15, 25.75, 22.30, 21.76, 13.86.

Alternatively, Compound 1 was prepared by slowly adding 1,8-diazabicyclo [5.4.0] undec-7-ene (DBU, 0.79 g, 5.2 mmol) to a solution of trans-delta-damascone (21.00 g, 109.4 mmol) and 1,8-dimercapto-3,6-dioxaoctane (10.00 g, 52.1 mmol) in tetrahydrofuran (THF, 100 mL). After stirring at room temperature for 18 h, n-heptane (100 mL) was added and the mixture treated with an aqueous solution of HCl (10%, 100 mL) and washed with a saturated aqueous solution of NaCl (2×100 mL). The organic layer was dried ($Na_2SO_4$), filtered and concentrated. Bulb-to-bulb distillation (120° C., 0.08 mbar, 2 h) to remove remaining volatiles afforded 27.87 g (99%) of Compound 1.

Alternatively, Compound 3 was prepared by stirring (E)-2-octen-4-one (31.6 g, 250.4 mmol) and 1,8-dimercapto-3,6-dioxaoctane (2,2'-(ethylenedioxy)diethanethiol, 21.8 g, 113.7 mmol) at room temperature for 28 d. Bulb-to-bulb distillation (100° C., 0.04 mbar) to remove remaining volatiles yielded 51.28 g (quant.) of Compound 3.

(b) Synthesis of (±)-2,2'-(3,6-dioxaoctane-1,8-diyl-bis(sulfanediyl))bis(octan-4-one) (Compound 3) and (±)-2-((2-(2-(2-mercaptoethoxy)ethoxy)ethyl)thio) octan-4-one (Compound 4)

(E)-2-Octen-4-one (3.75 g, 29.7 mmol) and 1,8-dimercapto-3,6-dioxaoctane (3.61 g, 19.8 mmol) were stirred at room temperature for 9 d. Column chromatography ($SiO_2$, n-heptane/ethyl acetate 4:1 and n-heptane/ethyl acetate 3:2) afforded 1.37 g of a mixture of Compound 3 and Compound 4 in a ratio of 35:65. The compounds can be used directly as a mixture. Further reversed-phase column chromatography (RP Vydac 218TP C18, water/acetonitrile 7:3 and water/acetonitrile 6:4) afforded 0.89 g of Compound 4.

$^1$H-NMR (Compound 4): 3.67-3.59 (m, 8 H), 3.36-3.26 (m, 1 H), 2.77-2.67 (m, 5 H), 2.57-2.49 (m, 1 H), 2.46-2.35 (m, 2 H), 1.63-1.51 (m, 3 H), 1.36-1.25 (m, 2 H), 1.28 (d, J=6.7, 3 H), 0.91 (t, J=7.3, 3 H).
$^{13}$C-NMR (Compound 4): 208.91, 72.93, 71.04, 70.29, 70.21, 50.06, 43.35, 35.38, 30.20, 25.74, 24.27, 22.30, 21.76, 13.86.

(c) Synthesis of (±)-3,3'-(3,6-dioxaoctane-1,8-diyl-isulfonyl)bis(1-(2,6,6-trimethylcyclohex-3-en-1-yl) butan-1-one) (Compound 5)

A solution of Oxone (2 $KHSO_5$/$KHSO_4$/$K_2SO_4$, 64.1 g, 421.4 mmol, 9.8 eq.) in water (220 mL) was added dropwise to a stirred solution of (±)-3,3'-(3,6-dioxaoctane-1,8-diylbis (sulfanediyl))bis(1-(2,6,6-trimethylcyclohex-3-en-1-yl)butan-1-one) (Compound 1, 24.4 g, 43.0 mmol) in methanol (330 mL), which was cooled to 1° C. on an ice bath. After the introduction, the ice bath was removed, and the suspension continued stirring for 18 h. The reaction mixture was extracted with ethyl acetate (350 mL), washed with a saturated aqueous solution of NaCl (200 mL), deionized water (200 mL), a saturated aqueous solution of $NaHCO_3$ (200 mL) and a saturated aqueous solution of NaCl (200 mL). The aqueous phases were each re-extracted with ethyl acetate (250 mL). The combined organic phases were dried ($Na_2SO_4$), filtered and concentrated. Drying under high vacuum (0.51 mbar) at 50° C. for 5 h afforded 25.05 g (81%) of Compound 5 as a mixture of two pairs of diastereoisomers (ca. 1.5:1), which can be used as such. Column chromatography of 1.0 g ($SiO_2$, n-heptane/ethyl acetate 9:1, then 8:2, then 7:1, then 1:1) afforded 0.49 g (45%) of an analytically pure sample.

$^1$H-NMR (major isomers): 5.59-5.51 (m, 2 H), 5.48-5.42 (m, 2 H), 4.01-3.87 (m, 4 H), 3.87-3.76 (m, 2 H), 3.69-3.62 (m, 4 H), 3.48-3.37 (m, 2 H), 3.22-3.05 (m, 4 H), 2.85 (ddd, J=18.9, 10.3, 1.2 Hz, 2 H), 2.57-2.45 (m, 2 H), 2.29 (d, J=10.6 Hz, 2 H), 2.03-1.93 (m, 2 H), 1.76-1.67 (m, 2 H), 1.39 (t, J=6.4 Hz, 6 H), 0.98 (s, 6 H), 0.95 (s, 6 H), 0.90 (d, J=6.7 Hz, 6 H).
$^{13}$C-NMR (major isomers): 210.53 and 210.50, 131.47 and 131.46, 124.21 and 124.20, 70.50, 64.69, 63.01 and 62.99, 53.95, 50.74 and 50.72, 45.65 and 45.47, 41.57, 33.43, 31.63, 29.78, 20.74, 19.90, 14.11.
$^1$H-NMR (minor isomers): 5.59-5.51 (m, 2 H), 5.48-5.42 (m, 2 H), 4.01-3.87 (m, 4 H), 3.87-3.76 (m, 2 H), 3.69-3.62 (m, 4 H), 3.48-3.37 (m, 2 H), 3.35-3.28 (m, 2 H), 3.22-3.10 (m, 2 H), 2.62 (dd, J=18.9, 9.9 Hz, 2 H), 2.29 (d, J=10.6 Hz, 2 H), 2.03-1.93 (m, 2 H), 1.76-1.67 (m, 2 H), 1.39 (t, J=6.4 Hz, 6 H), 0.99 (s, 6 H), 0.95 (s, 6 H), 0.90 (d, J=6.7 Hz, 6 H), 1.01-0.92 (m, 2 H).
$^{13}$C-NMR (minor isomers): 210.73 and 210.69, 131.42, 124.42, 70.53, 64.66, 63.33 and 63.31, 53.98, 50.75 and 50.69, 45.74 and 45.56, 41.57, 33.04, 32.08, 29.73, 20.77, 19.90, 13.92 and 13.91.

(d) Synthesis of (±)-2,2'-(3,6-dioxaoctane-1,8-diyld-isulfonyl)bis(octan-4-one) (Compound 6)

A solution of Oxone (2 $KHSO_5$/$KHSO_4$/$K_2SO_4$, 103.0 g, 676.5 mmol, 9.8 eq.) in water (400 mL) was added dropwise to a mechanically stirred solution of (±)-2,2'-(3,6-dioxaoctane-1,8-diylbis(sulfanediyl))bis(octan-4-one) (Compound 3, 30.0 g, 69.0 mmol) in methanol (500 mL), which was cooled to 1° C. on an ice bath. After the introduction, the ice bath was removed, and the suspension continued stirring for 18 h. The reaction mixture was filtered through sintered glass and rinsed with water (100 mL). The residue was taken up in ethyl acetate (300 mL), washed with demineralized water (200 mL), a saturated aqueous solution of $NaHCO_3$ (200 mL), and a saturated aqueous solution of NaCl (200 mL). The aqueous phases were each re-extracted with ethyl acetate (200 mL). The combined organic phases were dried ($Na_2SO_4$), filtered and concentrated. Drying under high vacuum (0.61 mbar) for 2 h afforded 16.3 g of a pair of diastereoisomers in a ratio of 3:1. The mother liquor obtained from the filtration through the sintered glass was concentrated to remove as much methanol as possible. The remaining water phase was extracted with ethyl acetate (2×, 200 mL). The organic phase was washed with demineralized water (200 mL), a saturated aqueous solution of $NaHCO_3$ (200 mL), and a saturated aqueous solution of NaCl (200 mL), and then dried ($Na_2SO_4$), filtered and concentrated. Drying under high vacuum (0.61 mbar) for 2 h afforded 17.4 g of a slightly yellow oil as the same pair of diastereoisomers in a ratio of 1:3, which slowly crystallized. The two product fractions were re-combined to afford Compound 6 as a mixture of diastereoisomers in a ratio of ca. 1:1.

$^1$H-NMR (600 MHz): 3.99-3.86 (m, 4 H), 3.86-3.77 (m, 2 H), 3.68-3.62 (m, 4 H), 3.42-3.33 (m, 2 H), 3.20-3.12 (m, 4 H), 2.61 (dd, J=18.1, 9.2, 2 H), 2.53-2.39 (m, 4 H), 1.62-1.52 (m, 4 H), 1.36-1.27 (m, 4 H), 1.36 and 1.35 (d, J=6.6, 6 H), 0.91 (t, J=7.3, 6 H).
$^{13}$C-NMR (151.0 MHz): 206.87 and 206.85, 70.52 and 70.50, 64.67, 54.24 and 54.22, 50.89 and 50.86, 43.18, 40.77 and 40.70, 25.81, 22.25, 14.02 and 13.98, 13.81.

(e) Synthesis of (±)-2,2'-(hexane-1,6-diylbis(sul-fanediyl))bis(octan-4-one) (Compound 7)

(E)-2-Octen-4-one (9.2 g, 73.2 mmol) and 1,6-hexanedi-thiol (5.0 g, 33.3 mmol) were stirred at room temperature for 48 d. Heating the reaction mixture at 50° C. under high vacuum (0.61 mbar) for 1 h to remove remaining volatiles yielded 12.6 g of the crude compound as a slightly yellow oil. Column chromatography of 2.0 g (SiO$_2$, n-heptane/ethyl acetate 9:1) afforded 1.38 g (65%) of Compound 7.
$^1$H-NMR: 3.30-3.20 (m, 2 H), 2.70 (dd, J=16.7, 5.8, 2 H), 2.57-2.48 (m, 6 H), 2.47-2.35 (m, 4 H), 1.63-1.50 (m, 8 H), 1.45-1.24 (m, 8 H), 1.27 (d, J=6.7, 6 H), 0.91 (t, J=7.4, 6 H).
$^{13}$C-NMR: 209.13, 50.11, 43.49, 35.10, 30.75, 29.56, 28.54, 25.75, 22.31, 21.73, 13.86.

(f) Synthesis of (±)-2,2'-(hexane-1,6-diyldisulfonyl) bis(octan-4-one) (Compound 8)

A solution of Oxone (2 KHSO$_5$/KHSO$_4$/K$_2$SO$_4$, 18.5 g, 121.7 mmol, 9.8 eq.) in water (45 mL) was added dropwise to a stirred solution of (±)-2,2'-(hexane-1,6-diylbis(sulfanediyl))bis(octan-4-one) (Compound 7, 5.0 g, 12.4 mmol) in methanol (75 mL), which was cooled to 1° C. on an ice bath. After the introduction, the ice bath was removed, and the suspension continued stirring for 18 h. The reaction mixture was extracted with ethyl acetate (200 mL), washed with a saturated aqueous solution of NaCl (100 mL), deionized water (100 mL), a saturated aqueous solution of NaHCO$_3$ (100 mL) and a saturated aqueous solution of NaCl (100 mL). The aqueous phases were each re-extracted with ethyl acetate (150 mL). The combined organic phases were dried (Na$_2$SO$_4$), filtered and concentrated. Drying under high vacuum (0.61 mbar) for 2 h afforded 4.73 g (81%) of Compound 8.
$^1$H-NMR: 3.66-3.57 (m, 2 H), 3.18 (dd, J=18.0, 4.2, 2 H), 2.94 (t, J=7.9, 4 H), 2.60 (dd, J=18.0, 8.7, 2 H), 2.55-2.40 (m, 4 H), 1.96-1.79 (m, 4 H), 1.65-1.46 (m, 8 H), 1.37 (d, J=7.1, 6 H), 1.37-1.28 (m, 4 H), 0.91 (t, J=7.4, 6 H).
$^{13}$C-NMR: 206.81, 52.66, 50.03, 43.07, 41.09, 28.07, 25.79, 25.25, 21.24, 14.47, 13.80.

(g) Synthesis of 4,4'-(3,6-dioxaoctane-1,8-diylbis (sulfanediyl))bis(4-methylpentan-2-one) (Compound 9)

DBU (0.87 g, 5.7 mmol) was slowly added to a solution of 4-methyl-3-penten-2-one (12.30 g, 125.5 mmol) and 1,8-dimercapto-3,6-dioxaoctane (10.40 g, 57.1 mmol) in THF (50 mL). After stirring at room temperature for 3 d, n-heptane (50 mL) was added. The mixture treated with an aqueous solution of HCl (10%, 50 mL) and washed with a saturated aqueous solution of NaCl (2×50 mL). The organic layer was dried (Na$_2$SO$_4$), filtered and concentrated. Bulb-to-bulb distillation (90° C., 0.05 mbar, 2 h) to remove remaining volatiles afforded 17.90 g (83%) of Compound 9.
$^1$H-NMR: 3.66-3.58 (m, 8 H), 2.77 (t, J=7.1, 4 H), 2.70 (s, 4 H), 2.19 (s, 6 H), 1.42 (s, 12 H).
$^{13}$C-NMR: 206.70, 70.86, 70.33, 54.61, 43.59, 32.33, 28.49, 27.85.

(h) Synthesis of 4-((6-mercaptohexyl)thio)-4-methylpentan-2-one (Compound 10) and 4,4'-(hexane-1, 6-diylbis(sulfanediyl))bis(4-methylpentan-2-one) (Compound 11)

DBU (0.52 g, 3.4 mmol) was slowly added to a solution of 4-methyl-3-penten-2-one (5.00 g, 51.0 mmol) and 1,6-hexanedithiol (10.00 g, 52.1 mmol) in THF (50 mL). After stirring at room temperature for 18 h, n-heptane (50 mL) was added and the mixture treated with an aqueous solution of HCl (10%, 50 mL) and washed with a saturated aqueous solution of NaCl (2×50 mL). The organic layer was dried (Na$_2$SO$_4$), filtered and concentrated. The compounds can be used directly as a mixture. Column chromatography (SiO$_2$, n-heptane/ethyl acetate 9:1) afforded 2.61 g (31%) of Compound 10 and 6.43 g (55%) of Compound 11.
$^1$H-NMR (Compound 10): 2.69 (s, 2 H), 2.57-2.49 (m, 4 H), 2.19 (s, 3 H), 1.68-1.52 (m, 4 H), 1.46-1.36 (m, 4 H), 1.42 (s, 6 H), 1.33 (t, J=7.7, 1 H).
$^{13}$C-NMR (Compound 10): 206.92, 54.70, 43.35, 33.80, 32.36, 29.35, 28.62, 28.52, 28.00, 27.94, 24.53.
$^1$H-NMR (Compound 11): 2.69 (s, 4 H), 2.54 (t, J=7.3), 4 H), 2.19 (s, 6 H), 1.62-1.52 (m, 4 H), 1.46-1.36 (m, 4 H), 1.42 (s, 12 H).
$^{13}$C-NMR (Compound 11): 206.92, 54.70, 43.35, 32.36, 29.36, 28.84, 28.52, 28.02.

(i) Synthesis of 3-((6-mercaptohexyl)thio)-1-(2,6,6-trimethylcyclohexa-1,3-dien-1-yl)butan-1-one (Compound 12), 3,3'-(hexane-1,6-diylbis(sulfanediyl))bis(1-(2,6,6-trimethylcyclohexa-1,3-dien-1-yl)butan-1-one) (Compound 13), 4-methyl-4-((6-((4-oxo-4-(2,6,6-trimethylcyclohexa-1,3-dien-1-yl) butan-2-yl)thio)hexyl)thio)pentan-2-one (Compound 14) and 4((6-mercaptohexyl)thio)-4-methylpentan-2-one (Compound 10)

(E)-1-(2,6,6-Trimethylcyclohexa-1,3-dien-1-yl)but-2-en-1-one (3.81 g, 20.0 mmol), 4-methyl-3-penten-2-one (1.96 g, 20.0 mmol) and 1,6-hexanedithiol (3.01 g, 20.0 mmol) were stirred at room temperature for 30 d. Column chromatography (SiO$_2$, n-heptane to n-heptane/ethyl acetate 95:5) afforded 0.44 g of a mixture of 1,6-hexanedithiol and Compound 12 (ca. 55:45), 0.85 g of a mixture of Compound 12 and Compound 13 (ca. 34:66) and 0.03 g of Compound 13. Further elution (n-heptane/ethyl acetate 9:1 to 1:1) afforded 0.13 g of a mixture of Compound 14 and Compound 10 (ca. 50:50).
$^1$H-NMR (Compound 12): 5.87-5.75 (m, 2 H), 3.40-3.31 (m, 1 H), 2.89 (dd, J=18.3, 4.8, 1 H), 2.72 (dd, J=18.6, 8.3, 1 H), 2.59-2.49 (m, 4 H), 2.11-2.06 (m, 2 H), 1.73 (s, 3 H), 1.66-1.56 (4 H), 1.45-1.37 (4 H), 1.34 (d, J=7.1, 3 H), 1.08 (s, 6 H).
$^{13}$C-NMR (Compound 12): 207.63, 141.55, 128.11, 127.72, 127.52, 52.94, 39.74, 34.27, 33.85, 33.85, 30.84, 29.54, 28.39, 27.93, 26.20 (2×), 24.54, 21.76, 19.10.
$^1$H-NMR (Compound 13): 5.87-5.75 (m, 4 H), 3.41-3.31 (m, 2 H), 2.89 (dd, J=18.3, 4.8, 2 H), 2.72 (dd, J=18.3, 8.3, 2 H), 2.55 (t, J=7.4, 4 H), 2.11-2.06 (m, 4 H), 1.73 (s, 6 H), 1.65-1.54 (m, 4 H), 1.45-1.37 (m, 4 H), 1.34 (d, J=6.7, 6 H), 1.08 (s, 12 H).
$^{13}$C-NMR (Compound 13): 207.63, 141.56, 128.11, 127.70, 127.50, 52.93, 39.74, 34.28, 33.85, 30.84, 29.58, 28.61, 26.21, 26.19, 21.74, 19.09. $^1$H-NMR (Compound 14): 5.87-5.81 (m, 1 H), 5.81-5.75 (m, 1 H), 3.41-3.31 (m, 1 H), 2.89 (dd, J=18.6, 4.8, 1 H), 2.72 (dd, J=18.6, 8.3, 1 H), 2.69 (s, 2 H), 2.59-2.49 (m, 4 H), 2.19 (s, 3 H), 2.11-2.07 (m, 2 H), 1.73 (s, 3 H), 1.66-1.53 (m, 4 H), 1.45-1.38 (m, 4 H), 1.42 (s, 6 H), 1.34 (d, J=6.7, 3 H), 1.08 (s, 6 H).
$^{13}$C-NMR (Compound 14): 207.63, 206.97, 141.55, 128.11, 127.72, 127.52, 54.71, 52.93, 43.35, 39.74, 34.27, 33.86, 32.37, 30.86, 29.55, 29.39, 28.84, 28.61, 28.51, 28.03, 26.20, 21.76, 19.10.

(j) Synthesis of (3R,3'R)-6,6'-((decane-1,10-diylbis (sulfanediyl))bis(propane-2,2-diyl))bis(3-methylcyclohexan-1-one) (Compound 15)

DBU (0.26 g, 1.7 mmol) was slowly added to a solution of (R)-5-methyl-2-(propan-2-ylidene)cyclohexan-1-one (5.60 g, 36.8 mmol) and 1,10-decanedithiol (3.45 g, 16.7 mmol) in THF (50 mL). After stirring at room temperature for 18 h, n-heptane (50 mL) was added and the mixture treated with an aqueous solution of HCl (10%, 50 mL) and washed with a saturated aqueous solution of NaCl (2×50 mL). The organic layer was dried ($Na_2SO_4$), filtered and concentrated to give 8.93 g of the crude compound. Column chromatography of 3.0 g ($SiO_2$, n-heptane/ethyl acetate 95:5) afforded 0.31 g (10%) of Compound 15 as a mixture of isomers (ca. 2:1).

$^1$H-NMR (major isomer): 2.61-2.39 (m, 8 H), 2.38-2.24 (m, 2 H), 2.08-2.00 (m, 2 H), 1.99-1.82 (m, 4 H), 1.59-1.49 (m, 6 H), 1.51 (s, 6 H), 1.42-1.33 (m, 6 H), 1.36 (s, 6 H), 1.33-1.22 (m, 8 H), 1.02 (d, J=6.4, 6 H).

$^{13}$C-NMR (major isomer): 210.82, 58.06, 52.43, 48.85, 36.71, 34.75, 29.66, 29.53, 29.43, 29.27 (2×), 27.93, 27.69, 23.96, 22.28.

$^1$H-NMR (minor isomer): 2.61-2.39 (m, 8 H), 2.38-2.24 (m, 4 H), 2.14-2.08 (m, 2 H), 1.99-1.82 (m, 4 H), 1.71-1.61 (m, 2 H), 1.59-1.49 (m, 4 H), 1.48 (s, 6 H), 1.42-1.33 (m, 4 H), 1.37 (s, 6 H), 1.33-1.22 (m, 8 H), 0.96 (d, J=7.1, 6 H).

$^{13}$C-NMR (minor isomer): 211.60, 58.24, 50.44, 47.00, 32.69, 31.45, 29.51, 29.43, 29.27 (2×), 28.32, 27.81, 25.53, 24.71, 19.29.

Example 2

Performance of a Model Surface Cleaner Comprising an Invention's Compound of Formula (I)—Comparison of the Fragrance Release from Monomeric and Dimeric Structures Compound 11 (76.8 mg) was dissolved in 2-propanol (0.2 mL). Then an aqueous solution of sodium lauryl ether sulfate (SLES 10%) was added to complete to 5 g, representing a simplified model surface cleaner formulation. An aliquot of this solution (90 mg) was spread onto a glass plate (2.5×7.5 cm) and dried for 24 h. The glass plate was then placed in a homemade headspace cell (ca. 625 mL inner volume), and a continuous flow of air (ca. 200 mL/min) was aspirated through the sampling cell. The air flow was passed through activated charcoal and through a saturated aqueous solution of NaCl to ensure a constant humidity of 75%. The volatiles were then alternatively adsorbed onto a waste Tenax® cartridge for 15 min and onto a clean Tenax® cartridge for another 15 min during 3 h (180 min) to collect a total of 6 data points. The waste cartridges were discarded; the other cartridges were desorbed on a Markes TD 100-XR desorber (at 280° C. for 10 min) and the volatiles injected into an Agilent Technologies 7890A gas chromatograph equipped with a Supelco SPB1 capillary column (30 m, i.d. 0.25 mm, film 0.25 μm) and coupled to an Agilent 5975C inert MSD mass spectrometer. The volatiles were eluted with a flow of He at 0.9 mL/min using a temperature gradient moving from 40° C. (for 1 min), to 180° C. at 10° C./min and to 260° C. at 30° C./min. Headspace concentrations (in ng/L air) were obtained by external standard calibrations using different concentrations of 4-methylpent-3-en-2-one as the fragrance to be released in ethanol. Each calibration solution (0.2 μL) was injected onto a clean Tenax® cartridge, which was desorbed and analyzed under the same conditions.

The same experiment was carried out using 4-(dodecylthio)-4-methylpentan-2-one as a reference compound. The synthesis of this compound has been described in the prior-art (J. R. Stephens, J. J. Hydock, M. P. Kleinholz, J. Am. Chem. Soc., 1951, 73, 4050).

The average headspace concentrations (mean values of the 6 data points) obtained from two measurements are listed in Table 1.

TABLE 1

Average headspace concentrations of fragrances released from compounds of formula (I) with respect to a prior-art reference compound on a glass plate after drying for 1 day.

| Compound | Concentration of 4-methylpent-3-en-2-one released [ng/L] | Increase of the release from the invention's compound with respect to the reference compound |
|---|---|---|
| Reference compound from the prior-art | 1.6 | ca. 33% |
| Compound 11 according to the present invention | 2.1 | |

"Dimeric" compounds according to formula (I) (with Q being a divalent hydrocarbon group) are thus more efficient in releasing fragrance raw materials than the corresponding "monomeric" analogues from the prior art (with Q being a monovalent hydrocarbon group).

Example 3

Performance of a Fabric Softener Base Comprising an Invention's Compound of Formula (I)

The generation of long-lasting fresh green, floral and fruity odors from the present invention's compounds of formula (I) was tested in a fabric softening surfactant emulsion with the following final composition:

| | |
|---|---|
| Stepantex ® VL90 A (origin: Stepan) | 12.21% by weight |
| Calcium chloride (10% aq. solution) | 0.40% by weight |
| Proxel ® GXL (origin: Avecia) | 0.04% by weight |
| Water | 87.35% by weight |

In a flask, a solution (0.1 mL) of one of the invention's compounds of formula (I) described in Example 1 (at an amount to release a total of 0.05 mmol of a given fragrance) in ethanol (10 mL) was added to the fabric softener (0.07 g) and diluted with demineralized cold tap water (23 g). The sample was vigorously shaken (10×). Then one cotton sheet (EMPA cotton test cloth Nr. 221, origin: Eidgenössische Materialprüfanstalt), pre-washed with an unperfumed detergent powder and cut to ca. 15×15 cm sheets, ca. 5.1 g) was added and agitated manually for 3 min, left standing for 2 min, then wrung out by hand, and weighed (ca. 10.0 g) to obtain a constant quantity of residual water. A reference sample (0.1 mL) consisting of an equimolar amount of unmodified fragrance (0.05 mmol) in ethanol (10 mL) was added to the fabric softener (0.07 g) in water (23 g) and analyzed the same way. The cotton sheets were line-dried for 1 or 3 days before being analyzed. For the measurements, the sheets were put into a headspace sampling cell (ca. 165 mL inner volume), which were thermostatted at 25° C. and exposed to a constant air flow of ca. 200 mL/min. The air was filtered through active charcoal and aspirated through a saturated solution of NaCl (to ensure a constant humidity of the air of ca. 75%). The system was equilibrated during 15 min while adsorbing the volatiles on a waste Tenax® cartridge (filled with 100 mg of Tenax® TA adsorbent resin). Then, seven times consecutively, the volatiles were adsorbed for 15 min on a clean Tenax® cartridge and for 45 min on a waste Tenax® cartridge. The waste cartridges were discarded; the other cartridges were desorbed on a Perkin Elmer TurboMatrix 350 desorber coupled to an Agilent Technologies 7890A gas chromatograph equipped with a HP-1 capillary column (30 m, i.d. 0.25 mm, film 0.25 μm) and an Agilent 5975C inert MSD spectrometer. The volatiles were eluted with helium (1 mL/min) using a temperature gradient moving from 60° C. (kept for 1 min) to 200° C. at 10° C./min. Alternatively, cartridges were desorbed on a Perkin Elmer TurboMatrix desorber coupled to an Agilent Technologies 7890A gas chromatograph with a HP-1 capillary column (30 m, i.d. 0.32 mm, film 0.25 μm) and a flame ionization detector. The volatiles were eluted with helium (1 mL/min) using a temperature gradient moving from 80° C. to 220° C. at 10° C./min. Headspace concentrations (in ng/L air) were obtained by external standard calibrations. Solutions of the fragrances to be released at different concentrations in ethanol were injected (0.2 μL) onto a clean Tenax® cartridge, which was desorbed and analyzed under the same conditions. The results obtained for the evaporation of the fragrances after a total sampling time of 150 min above dry cotton after line-drying for 1 and 3 days are summarized in Table 2. All data are average values of at least two measurements.

TABLE 2

Average headspace concentrations of fragrances released from compounds of formula (I) measured after sampling for 150 min on dry cotton after line-drying for 1 and 3 days.

| Compound | Concentration of (E)-2-octen-4-one (fruity strawberry odor) [ng/L] measured after line-drying for 1 day | Concentration of (E)-trans-1-(2,6,6-trimethylcyclohex-3-en-1-yl)but-2-en-1-one (rosy-fruity odor) [ng/L] measured after line-drying for 1 day |
|---|---|---|
| Reference | ca. 1.3 | ca. 0.1 |
| Compound 1 | — | 15.8 |
| Compound 2 | 18.3 | 11.9 |
| Compound 3 | 18.1 | — |
| Compound 3 & Compound 4 (9:1) | 20.6 | — |
| Compound 5 | — | 3.2 |
| Compound 6 | 7.8 | — |
| Compound 7 | 20.0 | — |
| Compound 8 | 5.3 | — |

| Compound | Concentration of (E)-2-octen-4-one (fruity strawberry odor) [ng/L] measured after line-drying for 3 days | Concentration of (E)-trans-1-(2,6,6-trimethylcyclohex-3-en-1-yl)but-2-en-1-one (fruity rosy odor) [ng/L] measured after line-drying for 3 days |
|---|---|---|
| Reference | ca. 0.7 | ca. 0.1 |
| Compound 1 | — | 12.8 |
| Compound 2 | 19.3 | 19.4 |
| Compound 3 | 16.5 | — |
| Compound 3 & Compound 4 (9:1) | 16.0 | — |
| Compound 5 | — | 1.5 |
| Compound 6 | 12.3 | — |
| Compound 7 | 15.3 | — |
| Compound 8 | 5.7 | — |

| Compound | Concentration of 4-methylpent-3-en-2-one (green, sweet honey-like odor) [ng/L] measured after line-drying for 1 day | Concentration of 5-methyl-2-(propan-2-ylidene)cyclohexan-1-one (herbaceous-minty odor) [ng/L] measured after line-drying for 1 day |
|---|---|---|
| Reference | ca. 0.6 | ca. 0.8 |
| Compound 9 | 3.0 | — |
| Compound 11 | 13.1 | — |
| Compound 15 | — | 4.8 |

The compounds according to formula (I) released higher amounts of fresh green, floral and fruity odors into the headspace above dry cotton than the reference sample with the unmodified fragrances. Compounds of formula (I) according to the present invention are thus capable of imparting long-lasting fresh green, floral and fruity odors to a cotton surface.

Example 4

Preparation of a Perfume Oil

A non-limiting example of a typical perfume oil is prepared by admixing the following perfuming co-ingredients:

| Ingredients | weight-% |
|---|---|
| Ethyl 2-methylbutanoate | 0.16 |
| Hexyl acetate | 0.37 |
| Limonene | 1.67 |
| 2,6-Dimethyl-7-octen-2-ol | 0.94 |
| 2-Phenylethanol | 2.15 |
| Linalool | 0.73 |
| (2RS,4SR/4RS)-4-Methyl-2-(2-methyl-1-propen-1-yl)tetrahydro-2H-pyran | 0.30 |
| Ethyl 2-methyl-1,3-dioxolane-2-acetate | 0.32 |
| Benzyl acetate | 2.46 |
| Allyl heptanoate | 0.38 |
| alpha-Terpineol | 0.88 |
| 3,7-Dimethyl-6-octen-1-ol | 0.55 |
| 4-Methoxybenzaldehyde | 1.00 |
| (E)-4-Methyl-3-decen-5-ol | 0.37 |
| [cis/trans-4-(2-Propanyl)cyclohexyl]methanol | 0.47 |
| 1-Methoxy-4-[(1E)-1-propen-1-yl]benzene | 0.15 |
| (1RS,2RS/2SR)-2-(2-Methyl-2-propanyl)cyclohexyl acetate | 1.95 |
| 1,1-Dimethyl-2-phenylethyl acetate | 0.95 |
| Tricyclo[5.2.1.0$^{2,\sim}$]dec-3/4-en-8-yl acetate | 3.34 |
| Allyl 3-cyclohexylpropanoate | 0.26 |
| 3-(4-Isopropylphenyl)-2-methylpropanal | 8.18 |
| (3E)-3-Methyl-4-(2,6,6-trimethyl-2-cyclohexen-1-yl)-3-buten-2-one and (1E)-1-(2,6,6-trimethyl-2-cyclohexen-1-yl)-1-penten-3-one | 1.13 |
| 2-Phenoxyethyl 2-methylpropanoate | 5.38 |
| Tricyclo[5.2.1.0(2,6)]dec-3/4-en-8-yl propanoate | 2.32 |
| 5-Heptyldihydro-2(3H)-furanone | 2.30 |
| 2/3-Methylbutyl salicylate | 1.42 |
| (3Z)-3-Hexen-1-yl salicylate | 0.31 |
| 1-(2,3,8,8-Tetramethyl-1,3,4,5,6,7-hexahydronaphthalen-2-yl)ethanone | 16.03 |
| Hexyl 2-hydroxybenzoate | 5.04 |
| (2E)-2-Benzylideneoctanal | 21.22 |
| (—)-(3aR,5aS,9aS,9bR)-3a,6,6,9a-Tetramethyldodecahydronaphtho[2,1-b]furan | 0.27 |
| Habanolide ® | 4.78 |
| Exaltolide ® | 3.82 |
| Benzyl 2-hydroxybenzoate | 3.01 |
| Dipropylene glycol | 5.39 |
| | Total: 100 |

Example 5

Preparation of Liquid Detergent Formulations Comprising an Invention's Compound of Formula (I)

A typical unperfumed liquid detergent formulation is listed in Table 3. A perfumed liquid detergent is prepared by adding, under gentle shaking, a perfume oil (0.3 to 0.8% by weight relative to the total weight of the liquid detergent) and at least one of the invention's compounds of formula (I) (0.05 to 1.0% by weight relative to the total weight of the liquid detergent) into the unperfumed liquid detergent formulation of Table 3.

TABLE 3

Composition of a typical unperfumed liquid detergent formulation

| Ingredients | Amount [wt %] |
|---|---|
| Sodium $C_{14-17}$ alkyl sec. sulfonate [1] | 7.0 |
| Fatty acids, $C_{12-18}$ and $C_{18}$-unsaturated [2] | 7.5 |
| $C_{12/14}$ fatty alcohol polyglycol ether with 7 mol EO [3] | 17.0 |
| Triethanolamine | 7.5 |
| Propylene glycol | 11.0 |
| Citric acid | 6.5 |
| Potassium hydroxyde | 9.5 |
| Properase ® L [4] | 0.2 |

TABLE 3-continued

Composition of a typical unperfumed liquid detergent formulation

| Ingredients | Amount [wt %] |
|---|---|
| Puradax ® EG L [4] | 0.2 |
| Purastar ® ST L [4] | 0.2 |
| Acrylates/Steareth-20 methacrylate structuring crosspolymer [5] | 6.0 |
| Deionized water | 27.4 |

[1] Hostapur ® SAS 60; origin: Clariant
[2] Edenor ® K 12-18; origin: Cognis
[3] Genapol ® LA 070; origin: Clariant
[4] Origin: Genencor International
[5] Aculyn ® 88; origin: Dow Chemicals

Example 6

Preparation of All-Purpose Cleaner Formulations Comprising an Invention's Compound of Formula (I)

A typical all-purpose cleaner formulation is listed in Table 4. A perfumed all-purpose cleaner is prepared by adding, under gentle shaking, a perfume oil (0.3 to 0.8% by weight relative to the total weight of the all-purpose cleaner) and at least one of the invention's compounds of formula (I) (0.05 to 0.8% by weight relative to the total weight of the all-purpose cleaner) into the unperfumed all-purpose cleaner formulation of Table 4.

TABLE 4

Composition of a typical unperfumed all-purpose cleaner formulation

| Ingredients | Amount [wt %] |
| --- | --- |
| Ethoxylated alcohol ($C_9$-$C_{11}$, 8 EO) [1] | 20.0 |
| Sodium dodecyl benzene sulfonate [2] | 16.0 |
| Sodiumcumene sulfonate [3] | 8.0 |
| Methyl chloro isothiazolinone/methyl isothiazolinone 3.3:1 [4] | 0.8 |
| Deionized water | 55.9 |

[1] Neodol ® 91-8; origin: Shell Chemicals
[2] Biosoft ® D-40; origin: Stepan
[3] Stepanate ® SCS; origin: Stepan
[4] Kathon ® CG; origin: Dow Chemicals

Example 7

Preparation of Transparent Isotropic Shampoo Formulations Comprising an Invention's Compound of Formula (I)

A typical unperfumed transparent isotropic shampoo formulation is listed in Table 5. The unperfumed shampoo formulation is prepared by dispersing Polyquaternium-10 in water. The remaining ingredients of Phase A are mixed separately by addition of one after the other while mixing well after each adjunction. This pre-mix is added to the Polyquaternium-10 dispersion and mixed for another 5 min. Then, the premixed Phase B and the premixed Phase C are added (Monomuls® 90L-12 is heated to melt in Texapon® NSO IS) while agitating. Phase D and Phase E are added while agitating. The pH is adjusted with a citric acid solution to 5.5-6.0 to give the unperfumed shampoo formulation listed in Table 5.

TABLE 5

Composition of a typical unperfumed transparent isotropic shampoo formulation

| Phase | Ingredients | Amount [wt %] |
| --- | --- | --- |
| A | Deionized water | 44.4 |
|   | Polyquaternium-10 [1] | 0.3 |
|   | Glycerin 85% [2] | 1.0 |
|   | DM DM Hydantoin [3] | 0.2 |
| B | Sodium laureth sulfate [4] | 28.0 |
|   | Cocamidopropyl betaine [5] | 3.2 |
|   | Disodium cocoamphodiacetate [6] | 4.0 |
|   | Ethoxy (20) stearyl alcohol [7] | 1.0 |
| C | Sodium laureth sulfate [4] | 3.0 |
|   | Glyceryl laureate [8] | 0.2 |
| D | Deionized water | 1.0 |
|   | Sodium methylparaben [9] | 0.1 |
| E | Sodium chloride (10% aqueous solution) | 15.0 |
|   | Citric acid (10% aqueous solution to pH 5.5-6.0) | q.s. |

[1] Ucare ® Polymer JR-400; origin: Noveon
[2] Origin: Brenntag Schweizerhall AG
[3] Glydant ®; origin: Lonza
[4] Texapon ® NSO IS; origin: Cognis
[5] Tego ® Betain F 50; origin: Evonik
[6] Amphotensid GB 2009; origin: Zschimmer & Schwarz
[7] Brij ® S20; origin: Croda
[8] Monomuls ® 90 L-12; origin: Gruenau GmbH
[9] Nipagin Monosodium; origin: NIPA The perfumed shampoo formulation is obtained by adding, under gentle shaking, a perfume oil (0.1 to 0.8% by weight relative to the total weight of the unperfumed shampoo formulation) and at least one of the compounds of formula (I) (0.05 to 0.5% by weight relative to the total weight of the unperfumed shampoo formulation) into the unperfumed shampoo formulation listed in Table 5.

Example 8

Preparation of Pearly Shampoo Formulations Comprising an Invention's Compound of Formula (I)

A typical unperfumed pearly shampoo formulation is listed in Table 6. The unperfumed shampoo formulation is prepared by dispersing Tetrasodium EDTA, Guar hydroxypropyltrimonium chloride and Polyquaternium-10 in water. NaOH (10% aqueous solution, Phase B) is added once Phase A is homogeneous. Then, the premixed Phase C is added, and the mixture heated to 75° C. Phase D ingredients are added and mixed until the mixture is homogeneous. The mixture is cooled. At 45° C., Phase E ingredients are added while mixing. The final viscosity is adjusted with NaCl (25% aqueous solution) and a pH of 5.5-6.0 is adjusted with NaOH (10% aqueous solution).

TABLE 6

Composition of a typical pearly shampoo formulation

| Phase | Ingredients | Amount [wt %] |
| --- | --- | --- |
| A | Deionized water | 45.97 |
|   | Tetrasodium EDTA [1] | 0.05 |
|   | Guar hydroxypropyl-trimonium chloride [2] | 0.05 |
|   | Polyquaternium-10 [3] | 0.075 |
| B | NaOH (10% aqueous solution) | 0.30 |
| C | Ammonium lauryl sulfate [4] | 34.00 |
|   | Ammonium laureth sulfate [5] | 9.25 |
|   | Cocamidopropyl betaine [6] | 2.00 |
|   | Dimethicone (&) $C_{12-13}$ pareth-4 (&) $C_{12-13}$ pareth-23 (&) salicylic acid [7] | 2.50 |
| D | Cetyl alcohol [8] | 1.20 |
|   | Cocamide MEA [9] | 1.50 |
|   | Glycol distearate [10] | 2.00 |

TABLE 6-continued

Composition of a typical pearly shampoo formulation

| Phase | Ingredients | Amount [wt %] |
|---|---|---|
| E | Methylchloroisothiazolinone & methylisothiazolinone [11] | 0.10 |
|  | D-Panthenol 75% [12] | 0.10 |
|  | Deionized water | 0.30 |
| F | Sodium chloride (25% aqueous solution) | 0.60 |

[1] EDETA ® B Powder; origin: BASF
[2] Jaguar ® C14S; origin: Rhodia
[3] Ucare ® Polymer JR-400; origin: Noveon
[4] Sulfetal ® LA B-E; origin: Zschimmer & Schwarz
[5] Zetesol ® LA; origin: Zschimmer & Schwarz
[6] Tego ® Betain F 50; origin: Evonik
[7] Xiameter ® MEM-1691; origin: Dow Corning
[8] Lanette ® 16; origin: BASF
[9] Comperlan ® 100; origin: Cognis
[10] Cutina ® AGS; origin: Cognis
[11] Kathon ® CG; origin: Rohm & Haas
[12] D-Panthenol; origin: Roche A perfumed pearly shampoo formulation is obtained by adding, under gentle shaking, a perfume oil (0.1 to 0.8% by weight relative to the total weight of the unperfumed shampoo formulation) and at least one of the compounds of formula (I) (0.05 to 0.5% by weight relative to the total weight of the unperfumed shampoo formulation) into the unperfumed pearly shampoo formulation listed in Table 6.

Example 9

Preparation of Rinse-Off Hair Conditioner Formulations Comprising an Invention's Compound of Formula (I)

A typical unperfumed rinse-off hair conditioner formulation is listed in Table 7. The unperfumed rinse-off hair conditioner formulation is prepared by mixing the ingredients of Phase A until an uniform mixture was obtained. Tylose® is allowed to completely dissolve. Then the mixture is heated to 70-75° C. The ingredients of Phase B are combined and melted at 70-75° C. Then the ingredients of Phase B are added to Phase A with good agitation, and the mixing is continued until that the mixture has a temperature of 60° C. Then, the ingredients of Phase C are added while agitating and keeping mixing until the mixture cooled to 40° C. The pH is adjusted with a citric acid solution to 3.5-4.0.

TABLE 7

Composition of a typical rinse-off hair conditioner formulation

| Phase | Ingredients | Amount [wt %] |
|---|---|---|
| A | Deionized water | 81.8 |
|  | Behentrimonium chloride [1] | 2.5 |
|  | Hydroxyethylcellulose [2] | 1.5 |
| B | Cetearyl alcohol [3] | 4.0 |
|  | Glyceryl stearate (and) PEG-100 stearate [4] | 2.0 |
|  | Behentrimonium metho-sulfate (and) cetyl alcohol (and) butylene glycol [5] | 4.0 |
|  | Ethoxy (20) stearyl alcohol [6] | 1.0 |

TABLE 7-continued

Composition of a typical rinse-off hair conditioner formulation

| Phase | Ingredients | Amount [wt %] |
|---|---|---|
| C | Amodimethicone (and) Trideceth-12 (and) Cetrimonium chloride [7] | 3.0 |
|  | Chlorhexidine digluconate (20% aqueous solution) [8] | 0.2 |
| D | Citric acid (10% aqueous solution tol pH 3.5-4.0) | q.s. |

[1] Genamin ® KDMP; origin: Clariant
[2] Tylose ® H10 Y G4; origin: Shin Etsu
[3] Lanette ® O; origin: BASF
[4] Arlacel ® 165; origin: Croda
[5] Incroquat ® Behenyl TMS-50-PA- (MH); origin: Croda
[6] Brij ® S20; origin: Croda
[7] Xiameter ® MEM-949; origin: Dow Corning
[8] Origin: Alfa Aesar A perfumed rinse-off hair conditioner formulation is obtained by adding, under gentle shaking, a perfume oil (0.2 to 1.0% by weight relative to the total weight of the unperfumed conditioner formulation) and at least one of the compounds of formula (I) (0.05 to 0.5% by weight relative to the total weight of the unperfumed conditioner formulation) into the unperfumed rinse-off hair conditioner formulation listed in Table 7.

Example 10

Preparation of Structured Shower Gel Formulations Comprising an Invention's Compound of Formula (I)

A typical unperfumed structured shower gel formulation is listed in Table 8. A perfumed structured shower gel is prepared by adding, under gentle shaking, a perfume oil (0.1 to 1.5% by weight relative to the total weight of the structured shower gel) and at least one of the invention's compounds of formula (I) (0.05 to 0.5% by weight relative to the total weight of the structured shower gel) into the unperfumed structured shower gel formulation of Table 8.

TABLE 8

Composition of a typical unperfumed structured shower gel formulation

| Ingredients | Amount [wt %] |
|---|---|
| Deionized water | 49.35 |
| Tetrasodium EDTA [1] | 0.05 |
| Acrylates co-polymer [2] | 6.00 |
| Sodium $C_{12-15}$ pareth sulfate [3] | 35.00 |
| Sodium hydroxide (20% aqueous solution) | 1.00 |
| Cocamidopropyl betaine [4] | 8.00 |
| Methylchloroisothiazolinone and methylisothiazolinone [5] | 0.10 |
| Citric acid (40% aqueous solution) | 0.50 |

[1] EDETA B powder; origin: BASF
[2] Carbopol Aqua SF-1 polymer; origin: Noveon
[3] Zetesol AO 328 U; origin: Zschimmer & Schwa
[4] Tego Betain F 50; origin: Goldschmidt
[5] Kathon ® CG; origin: Rohm & Haas Example 11

Preparation of Transparent Shower Gel Formulations Comprising an Invention's Compound of Formula (I)

A typical unperfumed transparent shower gel formulation is listed in Table 9. A perfumed transparent shower gel is prepared by adding, under gentle shaking, a perfume oil (0.5 to 1.5% by weight relative to the total weight of the transparent shower gel) and at least one of the invention's compounds of formula (I) (0.05 to 0.5% by weight relative to the total weight of the transparent shower gel) into the unperfumed transparent shower gel formulation of Table 9.

TABLE 9

Composition of a typical unperfumed transparent shower gel formulation

| Ingredients | Amount [wt %] |
|---|---|
| Deionized water | 52.40 |
| Tetrasodium EDTA [1] | 0.10 |
| Sodium benzoate | 0.50 |
| Propylene glycol | 2.00 |
| Sodium $C_{12-15}$ pareth sulfate [2] | 35.00 |
| Cocamidopropyl betaine [3] | 8.00 |
| Polyquaternium-7 [4] | 0.20 |
| Citric acid (40% aqueous solution) | 1.00 |
| Sodium chloride | 0.80 |

[1] EDETA B powder; origin: BASF
[2] Zetesol AO 328 U; origin: Zschimmer & Schwarz
[3] Tego Betain F 50; origin: Goldschmidt
[4] Merquat ® 550; origin: Lubrizol Example 12

Preparation of Milky Shower Gel Formulations Comprising an Invention's Compound of Formula (I)

A typical unperfumed milky shower gel formulation is listed in Table 10. A perfumed milky shower gel is prepared by adding, under gentle shaking, a perfume oil (0.1 to 1.5% by weight relative to the total weight of the milky shower gel) and at least one of the invention's compounds of formula (I) (0.05 to 0.5% by weight relative to the total weight of the milky shower gel) into the unperfumed milky shower gel formulation of Table 10.

TABLE 10

Composition of a typical unperfumed milky shower gel formulation

| Ingredients | Amount [wt %] |
|---|---|
| Deionized water | 50.95 |
| Tetrasodium EDTA [1] | 0.05 |
| Sodium benzoate | 0.50 |
| Glycerin (86% aqueous solution) | 3.50 |
| Sodium laureth sulfate [2] | 27.00 |
| Polyquaternium-7 [3] | 1.00 |
| Coco-betaine [4] | 6.00 |
| PEG-120 Methyl glucose trioleate [5] | 1.00 |
| Citric acid (40% aqueous solution) | 1.00 |
| Glycol distearate & laureth-4 & cocamidopropyl betaine [6] | 3.00 |
| Sodium chloride (20% aqueous solution) | 5.00 |
| PEG-40 hydrogenated castor oil [7] | 1.00 |

[1] EDETA ® B powder; origin: BASF
[2] Texapon ® NSO IS; origin: Cognis
[3] Merquat ® 550; origin: Lubrizol
[4] Dehyton ® AB-30; origin: Cognis
[5] Glucamate ® LT; origin: Lubrizol
[6] Euperlan ® PK 3000 AM; origin: Cognis
[7] Cremophor ® RH 40; origin: BASF Example 13

Preparation of Anhydrous Antiperspirant Spray Formulations Comprising an Invention's Compound of Formula (I)

A typical unperfumed anhydrous antiperspirant spray formulation is listed in Table 11. The anhydrous antiperspirant spray formulation is prepared by using a high speed stirrer. Silica and Quaternium-18-hectorite are added to the mixture of isopropyl myristate and cyclomethicone. Once completely swollen, aluminium chlorohydrate is added portion-wise under stirring until the mixture becomes homogeneous and without lumps.

TABLE 11

Composition of a typical unperfumed anhydrous antiperspirant spray

| Ingredients | Amount [wt %] |
|---|---|
| Cyclomethicone [1] | 53.51 |
| Isopropyl myristate | 9.04 |
| Silica [2] | 1.03 |
| Quaternium-18-hectorite [3] | 3.36 |
| Aluminium chlorohydrate [4] | 33.06 |

[1] Dow Corning ® 345 Fluid; origin: Dow Corning
[2] Aerosil ® 200 ; origin: Evonik
[3] Bentone ® 38; origin: Elementis Specialities
[4] Micro Dry Ultrafine; origin: Reheis The perfumed formulation is then obtained by adding a perfume oil (0.85% by weight relative to the total weight of the antiperspirant spray formulation) and at least one of the invention's compounds of formula (I) (0.15% by weight relative to the total weight of the antiperspirant spray formulation) into the unperfumed antiperspirant spray formulation of Table 11.

Example 14

Preparation of Deodorant Spray Emulsion Formulations Comprising an Invention's Compound of Formula (I)

A typical deodorant spray emulsion formulation is prepared by mixing and dissolving all the ingredients according to the sequence of Table 12. Then a perfume oil (1.35% by weight relative to the total weight of the deodorant spray formulation) and at least one of the invention's compounds of formula (I) (0.10-0.20% by weight relative to the total weight of the deodorant spray formulation) are added under gentle shaking. Then aerosol cans are filled, and the propellant is crimped and added. Aerosol filling: 40% active solution 60% propane/butane (2.5 bar).

TABLE 12

Composition of a typical unperfumed deodorant spray formulation

| Ingredients | Amount [wt %] |
|---|---|
| Ethanol (95%) | 90.65 |
| Triclosan [1] | 0.26 |
| Isopropyl myristate | 9.09 |

[1] Irgasan ® DP 300; origin: BASF

Example 15

Preparation of Deodorant Stick Formulations Comprising an Invention's Compound of Formula (I)

A typical deodorant stick formulation is obtained by weighing all the components of Part A (Table 13) and heating to 70-75° C. Ceteareth-25 is added once the other Part A ingredients are mixed and heated. When the Ceteareth-25 is dissolved, stearic acid is added. Part B is prepared by dissolving Triclosan in 1,2-propylene glycol (Table 13). Evaporated water is compensated. Then, slowly, under mixing, Part B is poured into Part A.

TABLE 13

Composition of a typical unperfumed deodorant stick formulation

| Phase | Ingredients | Amount [wt %] |
|---|---|---|
| A | Stearic acid | 5.05 |
|   | 1,2-Propylene glycol | 41.87 |
|   | Sodium hydroxide (20% aqueous solution) | 4.24 |
|   | Water | 30.30 |
|   | Tetrasodium EDTA [1] | 0.10 |
|   | Ceteareth-25 [2] | 1.52 |
|   | PPG-3 Myristyl ether [3] | 1.52 |
| B | 1,2-Propylene glycol | 15.14 |
|   | Triclosan [4] | 0.25 |

[1] Edeta ® B Power; origin: BASF
[2] Cremophor ® A25; origin: BASF
[3] Tegosoft ® APM; origin: Evonik
[4] Irgasan ® DP 300; origin: BASF A perfume oil (0.85% by weight relative to the total weight of the deodorant stick formulation) and at least one of the invention's compounds of formula (I) (0.10-0.20% by weight relative to the total weight of the deodorant stick formulation) are added under gentle shaking. To stock, a plastic bag is put into the bucket to be sealed after cooling. Moulds were filled at about 70° C.

Example 16

Preparation of Deodorant Roll-On Formulations Comprising an Invention's Compound of Formula (I)

A typical unperfumed deodorant roll-on formulation is listed in Table 14. Part A is prepared by sprinkling little-by-little the hydroxyethylcellulose into the water, whilst rapidly stirring with a turbine until the hydroxyethylcellulose is entirely swollen giving a limpid gel. Part B is slowly poured into Part A, whilst continuing stirring until the entire mixture is homogeneous. Then Part C is added.

TABLE 14

Composition of a typical unperfumed deodorant roll-on formulation

| Phase | Ingredients | Amount [wt %] |
|---|---|---|
| A | Water | 50.51 |
|   | Hydroxyethylcellulose [1] | 0.71 |
| B | Ethanol (95%) | 40.40 |
|   | 1,2-Propylene glycol | 5.05 |
|   | Triclosan [2] | 0.30 |
| C | PEG-40 hydrogenated castor oil [3] | 3.03 |

[1] Natrosol ®250 H; origin: Ashland
[2] Irgasan ® DP 300; origin: BASF
[3] Cremophor ® RH 40; origin: BASF The perfumed deodorant roll-on formulation is obtained by adding perfume oil (0.85% by weight relative to the total weight of the deodorant stick formulation) and at least one of the invention's compounds of formula (I) (0.10-0.20% by weight relative to the total weight of the deodorant stick formulation) under gentle shaking.

Example 17

Preparation of Day Cream Base O/W Emulsions Comprising an Invention's Compound of Formula (I)

A typical day cream base O/W emulsion formulation comprising an invention's compound of formula (I) is listed in Table 15. Phases A and B are heated separately to 70-75° C., then Phase A is added to Phase B and vacuum is applied. The mixture is stirred and cooled to 55° C. for 15 min. After cooling to room temperature, phenoxyethanol (and) piroctone olamine (Part C) are added when a temperature of 45° C. is reached. The mixture is stirred for 5 min before sodium carbomer (Part D), a perfume oil and at least one of the invention's compounds of formula (I) (Part E) are added. The mixture is stirred for 3 min, then the stirring was stopped for 15 min. When the temperature of the mixture reaches 30° C., the stirring is resumed for another 15 min until the cream becomes homogeneous, glossy and without lumps. If necessary the pH is adjusted to 6.70-7.20 with Glydant®, Phenoni®p or Nipaguard® PO5 or to 6.30-7.00 with Nikkoguard®.

TABLE 15

Composition of a typical day cream base O/W emulsion.

| Phase | Ingredients | Amount [wt %] |
|---|---|---|
| A | Steareth-2 (and) PEG-8 Distearate [1] | 5.0 |
|   | Cetyl alcohol | 0.5 |
|   | Ceteth-20 (AND) glyceryl stearate (and) PEG-6 stearate (and) Steareth-20 [2] | 4.0 |
|   | Squalan [3] | 1.0 |
|   | Paraffin oil [4] | 2.0 |
|   | Petrolatum [5] | 5.5 |

45

TABLE 15-continued

Composition of a typical day cream base O/W emulsion.

| Phase | Ingredients | Amount [wt %] |
|---|---|---|
| B | Deionized water | 75.9 |
|  | Propylene glycol | 5.0 |
| C | Phenoxyethanol (AND) Piroctone olamine [6] | 0.6 |
| D | Sodium carbomer [7] | 0.2 |
| E | Perfume oil | 0.15 |
|  | Compound of formula (I) | 0.15 |

[1] Arlacel ® 985; origin: Croda
[2] Tefose ®2561; origin: Gattefossé
[3] Biolip P 90; origin: Gattefossé
[4] Mineral oil 30-40 CPS
[5] Petroleum jelly
[6] Nipaguard ® PO 5; origin: Clariant
[7] PNC400

Example 18

Preparation of Hand Dishwash Formulations Comprising an Invention's Compound of Formula (I)

A typical unperfumed hand dishwash formulation is listed in Table 16. The unperfumed hand dishwash is prepared by mixing water with sodium hydroxide and diethanolamide. Then the linear alkylbenzene sulfonic acid is added. After neutralizing, the remaining ingredients are added and the pH is adjusted to 7-8 if necessary.

TABLE 16

Composition of a typical unperfumed hand dishwash formulation

| Ingredients | Amount [wt %] |
|---|---|
| Linear alkylbenzene sulfonic acid [1] | 20.0 |
| Diethanolamide [2] | 3.5 |
| Sodium hydroxide (50%) [3] | 3.4 |
| Secondary alcohol ethoxolate [4] | 2.5 |
| Sodium xylene sulfonate | 6.3 |
| Water | 64.3 |

[1] Biosoft ® S-118; origin: Stepan
[2] Ninol ® 40-CO; origin: Stepan
[3] Stepanate ® SXS; origin: Stepan
[4] Tergitol ® 15-S-9; origin: Dow Chemicals The perfumed hand dishwash formulation is obtained by adding perfume oil (0.85% by weight relative to the total weight of the hand dischwash formulation) and at least one of the invention's compounds of formula (I) (0.10-0.20% by weight relative to the total weight of the dishwash formulation) under gentle shaking.

The invention claimed is:

1. A compound of formula

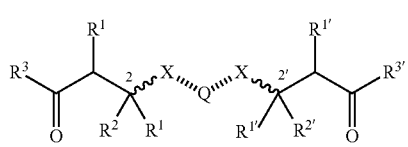

(I)

wherein $R^1$ and $R^{1'}$ represent independently from each other a hydrogen atom or a methyl group;

46 or, both $R^1$ and/or both $R^{1'}$, when taken together, represent a divalent $C_3$ to $C_8$ hydrocarbon group, $R^2$ represents a hydrogen atom or $C_1$ to $C_{12}$ hydrocarbon group and $R^{2'}$ represents a $C_1$ to $C_{12}$ hydrocarbon group, $R^3$ and $R^{3'}$ represent independently from each other a hydrogen atom or a $C_1$ to $C_{16}$ hydrocarbon group; or $R^1$ and $R^3$ and/or $R^{1'}$ and $R^{3'}$, when taken together, represent a divalent $C_2$ to $C_{12}$ hydrocarbon group, Q represents a divalent $C_4$ to $C_{18}$ hydrocarbon group, optionally comprising one to eight ether groups and/or one or two functional groups selected from the group consisting of alcohol, ketone, aldehyde, thioether, carboxylic acid, alkali carboxylate, amine, amide, carbamate, nitrile and thiol;

each X represents independently of each other either one of the groups of formulae (i) to (iii)

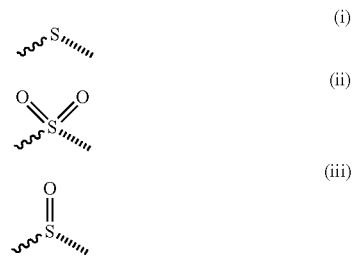

wherein the wavy line indicates a location of a bond between carbons 2 or 2' and X and the hatched line indicates a location of a bond between X and Q, provided that the hatched line is not directly linked to a heteroatom or to a carbonyl functional Q; and wherein the two X groups attached to Q are separated from each other by at least four carbon atoms and provided that 4,4'-(methylenebis(4,1-phenylenesulfonyl))bis(4-methylpentan-2-one) and 4,4'-([1,1'-biphenyl]-4,4'-disulfonyl)bis(4-methylpentan-2-one) are excluded.

2. The compound according to claim 1, wherein $R^1$ and $R^{1'}$ represent a hydrogen atom or a methyl group, $R^2$ and $R^{2'}$ represent a methyl or an ethyl group and $R^3$ and $R^{3'}$ represent a hydrogen atom or a $C_1$ to $C_{10}$ hydrocarbon group; or $R^1$ and $R^3$ and/or $R^{1'}$ and $R^{3'}$, when taken together represent a divalent $C_2$ to $C_6$ hydrocarbon group, X represents the groups of formula (i) and/or (ii) and Q represents a divalent $C_4$ to $C_{16}$, optionally comprising one to four ether groups and/or with one or two functional groups selected from the group consisting of alcohol, amine and carbamate.

3. The compound according to claim 1, wherein Q is selected from the group consisting of divalent butyl, pentyl, hexyl, heptyl, octyl, nonyl, decyl, undecyl, dodecyl, 3-oxapentyl, 3,6-dioxaoctyl, 3,6,9-trioxaundecyl, and 3,6,9,12-tetraoxatetradecyl.

4. The compound according to claim 1, wherein the compound of formula (I) is a compound of formula 5. The compound according to claim 1, wherein the compound of formula (I) is a compound of formula

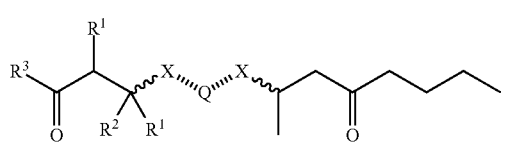
(I^a)

6. The compound according to claim 1, wherein the compound of formula (I) is a compound of formula

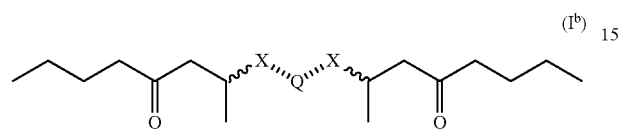
(I^b)

7. The compound according to claim 1, wherein the compound of formula (I) is a compound of formula

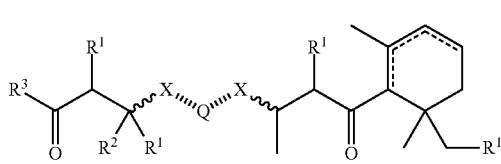
(I^c)

wherein the dotted lines represent a location of a single or a double bond.

8. The compound according to claim 1, wherein the compound of formula (I) is a compound of formula

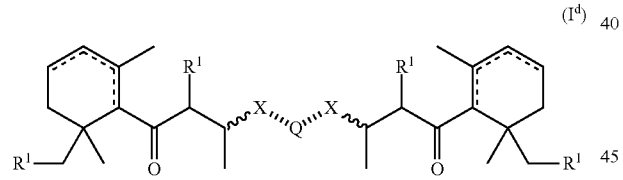
(I^d)

wherein the dotted lines represent a location of a single or a double bond.

9. The compound according to claim 1, wherein the compound of formula (I) is a compound of formula

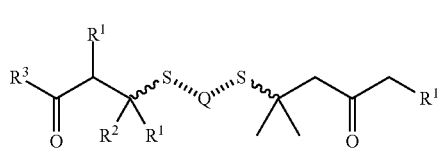
(I^e)

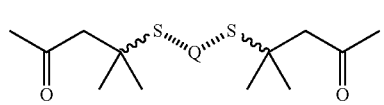
(I^f)

10. A method to confer, enhance, improve or modify fresh green, floral and/or fruity odor properties of a perfuming composition or of a perfumed article, which method comprises adding to said composition or article an effective amount of at least a compound of formula (I) according to claim 1.

11. A perfuming composition comprising:
  i) as perfuming ingredient, at least one compound of formula (I) according to claim 1;
  ii) at least one ingredient selected from the group consisting of a perfumery carrier and a perfumery base; and
  iii) optionally at least one perfumery adjuvant.

12. A perfumed consumer product comprising, as perfuming ingredient, at least one compound of formula (I) according to claim 1.

13. The perfumed consumer product according to claim 12, wherein the perfumed consumer product is a perfume, a fabric care product, a body-care product, an air care product, or a home care product.

14. A method of imparting a long-lasting or substantive fresh green, floral and/or fruity odor to surfaces, the method comprising adding at least one compound of formula (I) according to claim 1 to perfuming compositions or perfumed articles and applying them to a corresponding targeted surface.

15. The perfumed consumer product according to claim 12, wherein the perfumed consumer product is a fine perfume, a liquid or solid detergent, a fabric softener, a fabric refresher, an ironing water, a shampoo, a coloring preparation, a hair spray, a deodorant or antiperspirant, a perfumed soap, shower or bath mousse, oil or gel, a hygiene product, an air freshener, a "ready to use" powdered air freshener, or a hard-surface detergent.

16. A perfumed consumer product comprising the perfuming composition according to claim 11.

17. The perfumed consumer product according to claim 15, wherein the perfumed consumer product is a perfume, a fabric care product, a body-care product, an air care product, or a home care product.

18. The perfumed consumer product according to claim 15, wherein the perfumed consumer product is a fine perfume, a liquid or solid detergent, a fabric softener, a fabric refresher, an ironing water, a shampoo, a coloring preparation, a hair spray, a deodorant or antiperspirant, a perfumed soap, shower or bath mousse, oil or gel, a hygiene product, an air freshener, a "ready to use" powdered air freshener, or a hard-surface detergent.

19. The method of claim 14, wherein the surfaces are hard surfaces, fabric, skin, or hair.

20. The compound according to claim 1, wherein
  $R^1$ and $R^{1'}$ represent a hydrogen atom or a methyl group,
  $R^2$ and $R^{2'}$ represent a methyl or an ethyl group and
  $R^3$ and $R^{3'}$ represent a hydrogen atom or a $C_1$ to $C_{10}$ hydrocarbon group; or $R^1$ and $R^3$ and/or $R^{1'}$ and $R^{3'}$, when taken together represent a divalent $C_2$ to $C_6$ hydrocarbon group, X represents groups of formula (i) and/or (ii) and
Q represents a $C_4$ to $C_{16}$ alkyl or alkenyl group, optionally comprising one to four ether groups and/or with one or two functional groups selected from the group consisting of ester, alcohol, amine and carbamate.

\* \* \* \* \*